United States Patent
Conforti et al.

(10) Patent No.: US 9,777,279 B2
(45) Date of Patent: Oct. 3, 2017

(54) METHODS AND COMPOSITIONS FOR TREATING AUTOIMMUNE DISORDERS BY TARGETING KV1.3 ION CHANNELS WITH FUNCTIONALIZED LIPID-DERIVED NANOVESICLES

(71) Applicants: University of Cincinnati, Cincinnati, OH (US); North Carolina Agricultural and Technical State University, Greensboro, NC (US)

(72) Inventors: Laura Conforti, Wyoming, OH (US); Yeoheung Yun, Greensboro, NC (US)

(73) Assignees: University of Cincinnati, Cincinnati, OH (US); North Carolina Agricultural and Technical State University, Greensboro, NC (US)

( * ) Notice: Subject to any disclaimer, the term of this patent is extended or adjusted under 35 U.S.C. 154(b) by 0 days.

(21) Appl. No.: 14/863,525

(22) Filed: Sep. 24, 2015

(65) Prior Publication Data

US 2016/0160220 A1  Jun. 9, 2016

Related U.S. Application Data

(60) Provisional application No. 62/054,491, filed on Sep. 24, 2014.

(51) Int. Cl.

| | |
|---|---|
| *C07H 21/02* | (2006.01) |
| *C07H 21/04* | (2006.01) |
| *C12N 15/113* | (2010.01) |
| *A61K 31/713* | (2006.01) |
| *A61K 9/00* | (2006.01) |
| *A61K 47/48* | (2006.01) |
| *A61K 9/127* | (2006.01) |
| *C07K 16/28* | (2006.01) |

(52) U.S. Cl.
CPC ........ *C12N 15/1138* (2013.01); *A61K 9/0019* (2013.01); *A61K 9/1272* (2013.01); *A61K 31/713* (2013.01); *A61K 47/48823* (2013.01); *C07K 16/289* (2013.01); *C12N 2310/14* (2013.01); *C12N 2320/32* (2013.01)

(58) Field of Classification Search
CPC .......................... A61K 2300/00; C12N 15/113
See application file for complete search history.

(56) References Cited

U.S. PATENT DOCUMENTS

| | | | |
|---|---|---|---|
| 2007/0031844 A1* | 2/2007 | Khvorova ............ | A61K 31/713 435/6.11 |
| 2008/0113351 A1* | 5/2008 | Naito ................... | A61K 31/713 435/6.11 |
| 2010/0239562 A1* | 9/2010 | Nath ..................... | G01N 33/502 424/130.1 |
| 2010/0330156 A1* | 12/2010 | Liu ....................... | C07D 241/38 424/450 |

FOREIGN PATENT DOCUMENTS

WO    WO 2010/039742 A2 *   4/2010   ............. A61K 48/00

OTHER PUBLICATIONS

Paz, Z. and G.C. Tsokos, 2013, Curr Opin Rheumatol 25:297-303.
Hajdu, P. A.A. Chimote, T.H. Thomason, Y. Koo, Y.Yun, and L. Conforti, 2013, "Functionalized liposomes loaded with siRNAs targeting ion channels in effector memory T cells as a potential therapy for autoimmunity," Biomaterials 34: 10249-10257.
"The functional network of ion channels in T lymphocytes," Immunol Rev 231:59-87.
"Application of poly(ethylene glycol)-distearoylphosphatidylethanolamine (PEG-DSPE) block copolymers and their derivatives as nanomaterials in drug delivery," Int J Nanomedicine, 2012; 7: 4185-4198.
Sui G., Soohoo et al (2002) A DNA vector-based RNAi technology to suppress gene expression in mammalian cells, Proc Natl Acad Sci USA 99: 5515-5520.
Brummelkamp TR et al (2002) a system for stable expression of short interfering RNAs in mammalian cells. Science 296: 550-553.
Paul CP et al (2002) Effective expression of small interfering RNA in human cells. Nature Biotechnology 20: 505-508.

* cited by examiner

*Primary Examiner* — Amy Bowman
(74) *Attorney, Agent, or Firm* — Dinsmore & Shohl LLP

(57) ABSTRACT

Synthesis and pharmaceutical compositions of antibody-functionalized nanovesicles encapsulating ion channel knockout siRNA, and methods of treating autoimmune diseases associated with increased expression and/or hyperactivity of T cells by selectively targeting memory T cells with the nanoparticles, which deliver their siRNA cargo into the cytosol of the $T_M$ cell thus reducing ion channel expression and decreasing $Ca^{2+}$ influx.

8 Claims, 21 Drawing Sheets

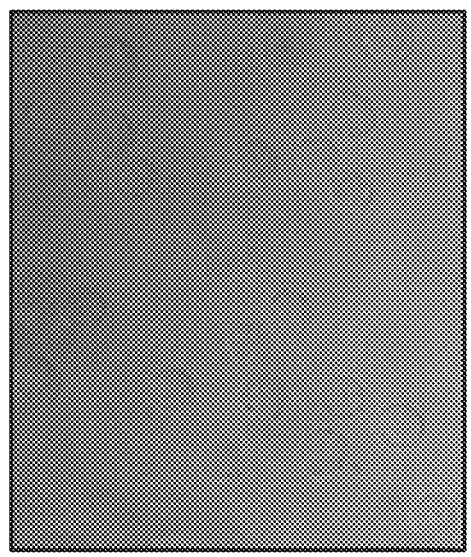
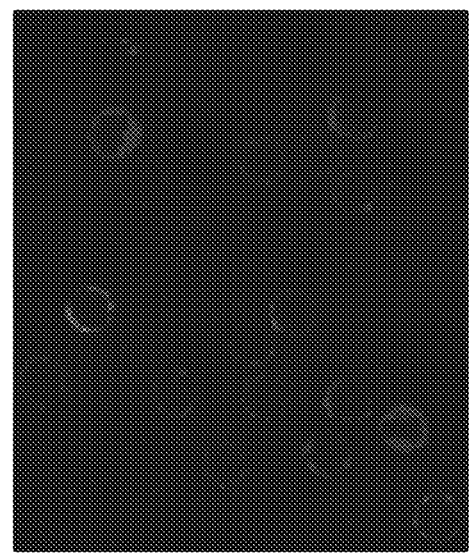
FIG. 2A    FIG. 2B
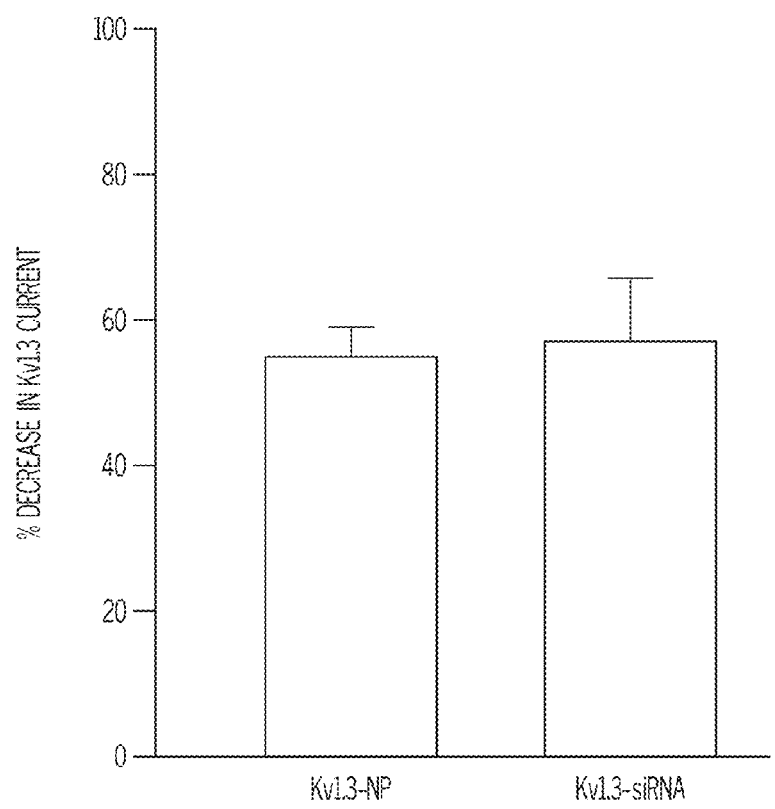
FIG. 3

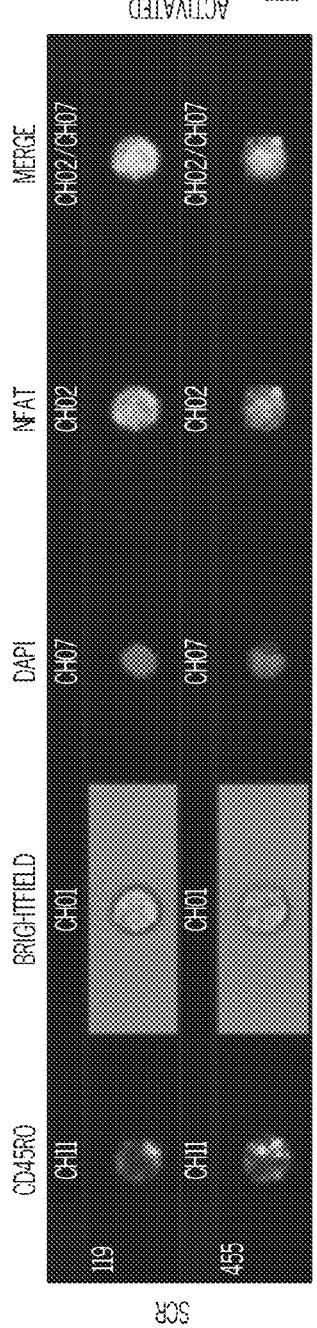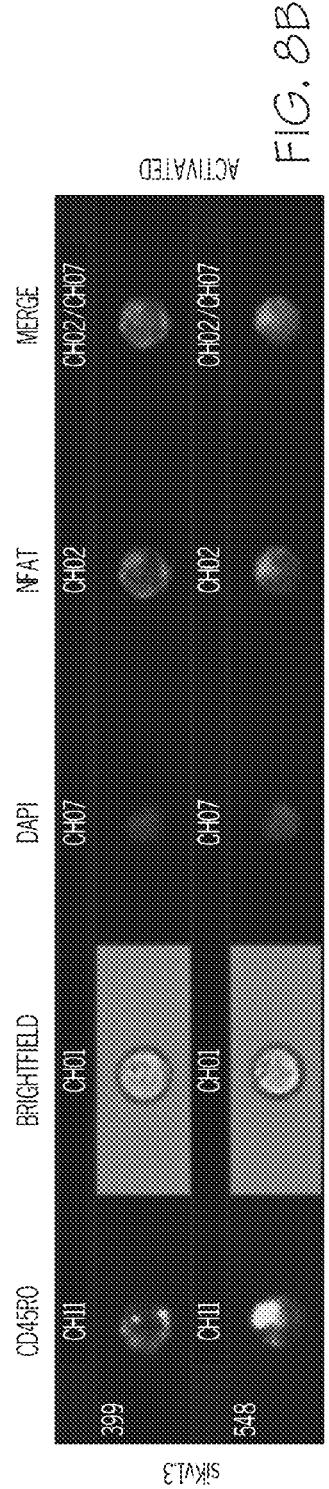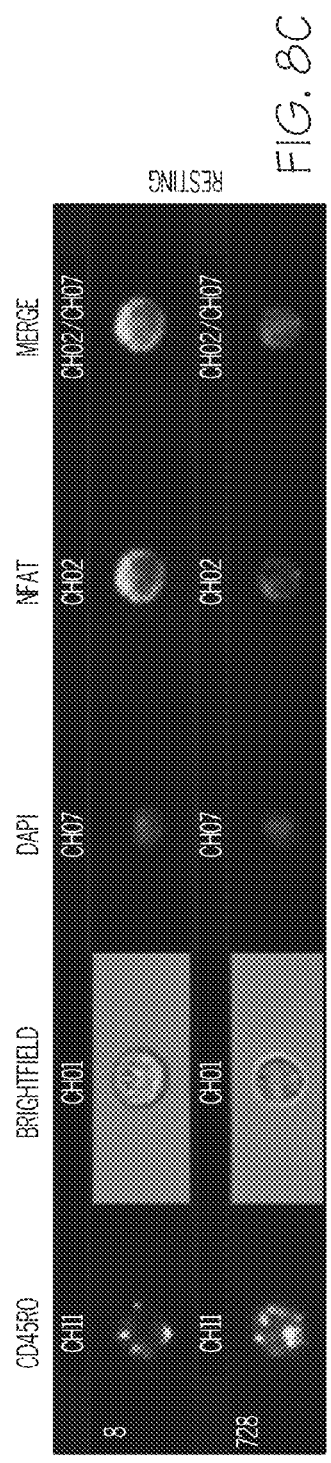

METHODS AND COMPOSITIONS FOR TREATING AUTOIMMUNE DISORDERS BY TARGETING KV1.3 ION CHANNELS WITH FUNCTIONALIZED LIPID-DERIVED NANOVESICLES

PRIORITY CLAIM

This application claims priority under 35 U.S.C. §119(e) to U.S. Provisional application No. 62/054,491 filed Sep. 24, 2014, the entire disclosure of which is incorporated herein by this reference.

GOVERNMENT LICENSE RIGHTS

This invention was made with government support under Contract No. 1R21AR060966 awarded by the National Institute of Health. The government has certain rights in the invention."

TECHNICAL FIELD

The presently disclosed subject matter relates to pharmaceutical compositions and methods effective for treatment of autoimmune disorders.

BACKGROUND

Appropriate functioning of the immune system is necessary to identify and eliminate pathogens and malfunctioning/cancerous cells. However, recognition of various proteins, small DNA-sequences or other molecules produced by the host body (termed self) as possible pathogenic agents leads to the onset of chronic diseases of the immune system named autoimmune diseases. The immune system is comprised of a variety of T cell subsets, which are responsible for the acquired immune defense. Naïve T cells are those that have never encountered an antigen, while central memory ($TC_M$) and effector memory ($TE_M$) cells were previously exposed to a specific antigen, and provide the memory response. $TE_M$ are capable of delivering immediate local tissue responses to antigens on the basis of their reduced activation requirements and increased frequency. In contrast, $TC_M$ cells (which constitute ca. 5% of the total memory pool) are capable of rapidly generating a large number of effector cells based on their high proliferative capacity and ability to differentiate into effectors.

The pathology of several autoimmune disorders (such as Multiple Sclerosis (MS), Type 1 Diabetes Mellitus (T1DM), Rheumatoid Arthritis (RA) and Systemic Lupus Erythematosus (SLE)) has been coupled to the presence of $TE_M$ cells which, in the case of MS and RA, have been reported to infiltrate the target tissues and contribute to local tissue damage. For example, in SLE, $TE_M$'s are highly expressed and hyperactive, and are thought to contribute to the cardiovascular complications of the disease. Consequently, a therapeutic intervention suppressing the function of $TE_M$ may be beneficial in autoimmunity.

The activation and the subsequent effector functions of T cells, such as proliferation and cytokine release, are firmly linked to the sustained elevation of intracellular $Ca^{2+}$ concentration ($[Ca^{2+}]i$) triggered by the encounter with an antigen. $Ca^{2+}$ influx induced by antigen presentation occurs through CRAC (Calcium Release Activated $Ca^{2+}$) channels that work in concert with other ion channels, transporters and pumps. Particularly, to sustain the driving force for $Ca^{2+}$ ions through CRAC, two potassium channels, the voltage-gated Kv1.3 and the intracellular $Ca^{2+}$ activated KCa3.1, maintain the negative transmembrane potential. It was reported that these two K$^+$ channels are differentially expressed in T cell subsets. $TE_M$'s from patients with autoimmune diseases (RA, T1DM, MS) are characterized by the high level of Kv1.3 as compared to KCa3.1 channels, hence, the former dominantly regulates the $TE_M$ cells' membrane potential. Indeed, $Ca^{2+}$-dependent activation in these cells can be prevented by application of specific Kv1.3 blockers. The present investigators previously demonstrated that inhibition of Kv1.3 channels with a potent specific inhibitor (ShK from *Stichodactyla helianthus*, sea anemone) can hamper $Ca^{2+}$-signaling in SLE T cells.

The treatment of autoimmune diseases requires a very careful strategy, as the systemic application of various drugs can inhibit the function of cells other than the targeted immune cells, which results in ensemble immunosuppression. Several studies reported that blocking of the Kv1.3 channel function by specific peptide toxins and small-molecules in animal models in vivo can be used to inhibit effector functions as well as migration of $TE_M$ cells in induced autoimmune deficiencies. However, other cell types express Kv1.3 channels (macrophages, dendritic cell, adipose cells, olfactory neurons), thus raising the possibility of undesirable side effects. Over the past few years more and more papers have been published reporting cell-specific approaches using NPs that had demonstrated fewer or no side-effects as compared to the systemic application of drugs generally.

An exemplary autoimmune disorder is Systemic Lupus Erythematosus (SLE). Currently approved therapies have serious side effects and, in many cases, limited efficacy. Emerging new therapies still undergoing clinical trials focus on the regulation of T and B cell function (Paz, Z., and G. C. Tsokos. 2013, *Curr Opin Rheumatol* 25:297-303, the disclosure of which is incorporated herein by this reference). These cells, in fact, play an important role in the pathogenesis of SLE. In particular, autoantigen-specific memory T ($T_M$) cells infiltrate the tissues, secrete inflammatory cytokines and reactivate accumulating B cells through cytokine production and direct CD40L-CD40 binding.

The CD40-CD40L interaction plays a particularly important role in SLE patients because CD40L is overexpressed in these patients' T cells. CD40L is a member of the tumor necrosis factor (TNF) superfamily located on activated T cells, and binds its receptor, CD40, on the B cells. This interaction stimulates B cell activation which, in turn, leads to inflammatory cytokine release, autoantibody formation and end-stage organ damage. Importantly, $T_M$ cells guarantee life-long persistence of immune memory and long-lived active B cells. Therefore, it is widely accepted that lupus cannot be cured without disarming these cells. Therapeutic interventions aiming to interrupt the reciprocal interaction between B and T cells via the CD40-CD40L pathway have shown some efficacy in SLE patients; however an increased risk of thrombotic complications have unfortunately halted clinical trials (CD40L is expressed in platelets). Clearly, new ways of selectively targeting $T_M$ cells to disrupt the T-B communication pathways involved in lupus and other autoimmune disorders having similar etiological considerations are needed.

SUMMARY

Accordingly, the present investigators engineered functionalized lipid nanovesicles enclosing small interfering RNAs "(siRNA," short double stranded RNA molecules that can be used to knock down a specific gene) against ion channels expressed in immune cells. The surface of the lipid nanovesicles are functionalized with antibodies against membrane proteins expressed only in specific immune cell subsets. According to specific embodiments, lipid nanovesicles (as used herein, nanovesicle, nanoparticle and NP have equivalent scope) enclose siRNAs against Kv1.3 channels and are functionalized with a monoclonal antibody which recognizes the CD45RO isoform of $T_M$ lymphocytes (Kv1.3-NP) (Hajdu, P., A. A. Chimote, T. H. Thompson, Y. Koo, Y. Yun, and L. Conforti, 2013, Functionalized liposomes loaded with siRNAs targeting ion channels in effector memory T cells as a potential therapy for autoimmunity. *Biomaterials* 34:10249-10257, the entire disclosure of which is incorporated herein by this reference). The NPs are internalized into the cells, and their siRNA cargo is delivered into the cytosol. As a result, Kv1.3 channel expression is reduced, which in turn leads to decreased $Ca^{2+}$ influx. Embodiments of the invention offer novel compositions and methods for the treatment of autoimmune diseases which are associated to hyperactivity of T cells.

Some embodiments of the invention are directed to pharmaceutical compositions comprising antibody-functionalized lipid nanovesicles. The lipid nanovesicles comprise antibody selective for a membrane protein unique to a target subset of immune system cells and bound to a surface of the lipid nanovesicle; and siRNA effective for inhibiting expression of an ion channel of the target subset cells upon transfection. The siRNA is encapsulated within the lipid nanovesicle.

Other embodiments provide methods of treating a patient suffering from a condition of the immune system characterized by overexpressed and/or hyperexcitable immune system cells. The methods comprise administering a composition formulated to selectively bind to a target subset of the immune system cells and transfect it with siRNA. In certain aspects the composition comprises antibody-functionalized lipid nanovesicles. The antibody are selective for a membrane protein unique to the target subset of immune system cells and are bound to a surface of the lipid nanovesicle. The lipid nanovesicles are encapsulated with siRNA effective for inhibiting expression of an ion channel of the target subset cells upon transfection.

Methods of manufacturing an agent effective for the treatment of a chronic immune system disorder characterized by over-expression and/or hyperexcitability of immune system cells are also provided and comprise: identifying a membrane protein substantially unique to a target subset of the immune system cells; encapsulating siRNA effective for inhibiting an ion channel of the target subset cell into a lipid nanovesicle; and functionalizing a surface of the lipid nanovesicle with an antibody to the membrane protein.

Still other embodiments are directed to methods of treating a patient suffering from an immune system disorder characterized by hyperexcitable $T_M$ cells. Such methods comprise: selectively suppressing the function of $T_M$-cells and interrupting a CD40-CD40L pathway between B and T cells of the immune system. Selectively is defined in this context as substantially avoiding altering expression of non $T_M$-cells.

These and other embodiments and aspects of the invention we be further clarified and understood by reference to the Figures and Detailed Description herein.

BRIEF DESCRIPTION OF THE FIGURES

FIG. 2A. Confocal micrograph images of CD3 cells incubated with CD45RO-NPs (darker), and 2B) labeled with CD45RA antibody (lighter).

FIG. 3. Bar graph demonstrating decrease in Kv1.3 currents in CD3 cells incubated with Kv1.3-NPs.

FIG. 8A. Representative image of cells acquired by imaging flow cytometry showing activated cells treated with scr-NPs (top) or 8B) siKv.3-NPs (bottom), and 8C) resting T-cells treated with null-NPs and stained with NFAT (darker) and DAPI (lighter) where the nuclear translocation of NFAT is indicated by the colocalization of channels in the merged images.

DETAILED DESCRIPTION

Figure 1:
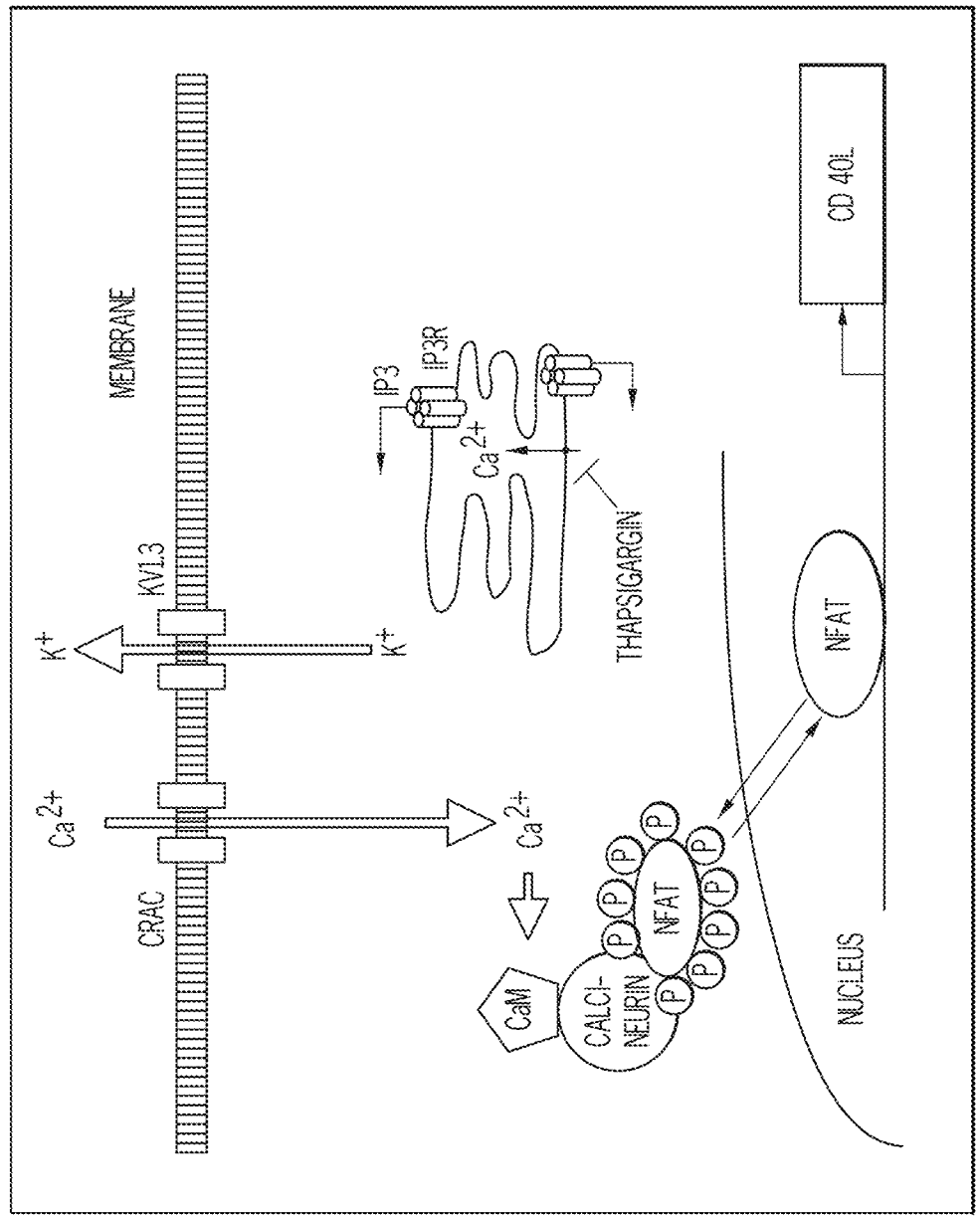
FIG. 1. Schematic representation of signaling pathway in an activated T-cell.
Figure 4:
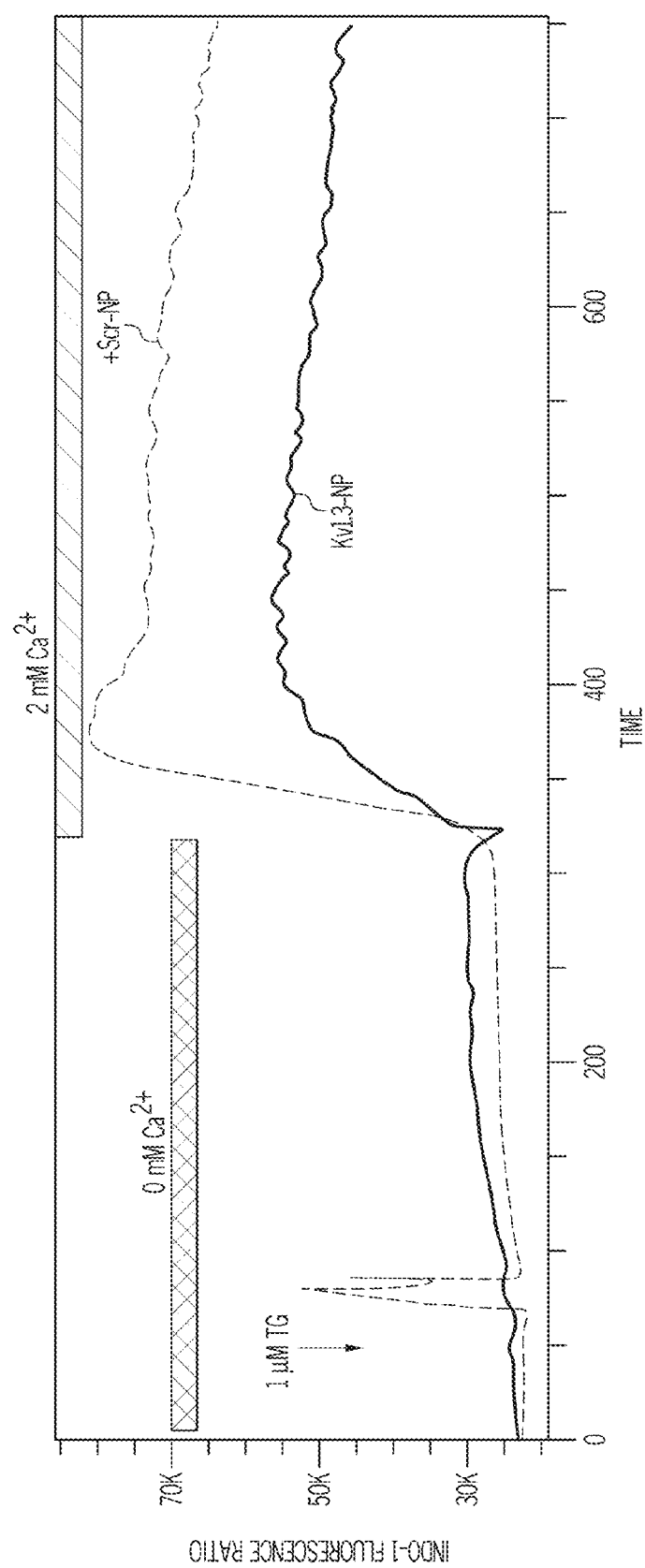
FIG. 4. Graphical representation of ion channel dependent $Ca^{2+}$ fluxes from CD3 cells incubated with either scr-NP or Kv1.3-NP.

The pathogenesis of many autoimmune disorders is characterized by hyperactive and/or over-expressed $T_M$ cells. SLE is a typical and therefore exemplary such autoimmune disorder. In SLE the $T_M$ cells show a $Ca^{2+}$-dependent increase in the costimulatory CD40 ligand (CD40L), which binds CD40 on B cells, resulting in B cell activation and autoantibody production. CD40L is widely recognized as a potential target for developing therapies for SLE. Cystolic $Ca^{2+}$ levels increase during T cell activation and mediate CD40L expression, and are regulated by Kv1.3 ion channels. As described in Cahalan, M. D., and K. G. Chandy, 2009, $Ca^{2+}$ signaling regulates the transcription factor NF-AT which drives both cytokine production and CD40L expression in T cells ("The functional network of ion channels in T lymphocytes," *Immunol Rev* 231:59-87, the entire disclosure of which is incorporated herein by this reference.) $Ca^{2+}$ signaling is controlled by ion channels. Inhibition of Kv1.3 channels is therefore a desired outcome of pharmacological therapies.

Although in vivo application of Kv1.3 blockers has been used effectively in animal models of autoimmunity, pharmaceutical therapeutics have been limited because the expression of Kv1.3 channels in other cell types often leads to unexpected and undesirable side effects. Targeted silencing of the Kv1.3 gene in $T_M$'s could be an alternative approach. Effective and selective in vivo delivery of siRNA, however, remains a challenge in the art. The present investigators therefore designed a novel therapy utilizing nanoparticles as selective siRNA delivery vehicles. The design takes advantage of the fact that $TE_M$'s are characterized by the presence of "O" or "0" isoform of CD45R (CD45RO phosphatase) and lack of CD45RA (isoform "A") and CCR7—(chemokine receptor 7) in the cell membrane. Also $TC_M$ are CD45RO+, however, they express CCR7 and make up a small fraction of memory T cell population. Naïve T cells, on the other hand, constitute a CD45RA+CCR7+ and CD45RO– subpopulation of the T cell pool.

CD45RO antibody-functionalized NPs encapsulated with siRNAs against Kv1.3 channels and selective to human CD45+, effector memory T cells were designed, synthesized, and tested for suppression of relevant function. Fluorescence confocal microscopy was utilized along with immucytochemistry to test if the binding and the internalization of CD45RO antibody labeled NPs, as well as the release of fluorophore-tagged siRNA into the cytosol, is specific to the target $T_M$ cells. Furthermore, to monitor the effectiveness of gene-down-regulation by siRNAs encapsulated into NPs, single-cell electrophysiology (patch-clamp technique) was utilized to determine the expression/current of Kv1.3 ion channels in $T_M$ cells. To assess the functional impact of Kv1.3 gene knock-down on the $Ca^{2+-}$ response in $T_M$ cells, Indo-1 ratiometric $Ca^{2+}$ measurements were taken using a flow cytometer.

As demonstrated by the Examples below, Kv1.3-NPs selectively targeted $T_M$ cells, and not naïve T cells. Kv1.3-NPs were effective in reducing NF-AT activation (nuclear translocation) and CD40L expression in healthy T cells. Furthermore, these Kv1.3-NPs corrected the CD40L overexpression of SLE $T_M$ cells. They delivered the encapsulated siRNAs into the targeted T cells where they suppressed Kv1.3 channel expression and $Ca^{2+}$ influx implicated in the pathology of SLE and other autoimmune disorders.

One embodiment of the invention is directed to pharmaceutical compositions. The compositions comprise antibody-functionalized lipid nanovesicles, wherein the antibody is a binding partner for a membrane protein unique to a target subset of immune system cells. The nanovesicles encapsulate siRNA effective for inhibiting expression of an ion channel of the target subset of cells upon transfection.

Methods for functionalizing lipid nanoparticles with antibody is known in the art. For example, guidance is provided by "Application of poly(ethylene glycol)-distearoylphosphatidylethanolamine (PEG-DSPE) block copolymers and their derivatives as nanomaterials in drug delivery" Int J Nanomedicine. 2012; 7: 4185-4198, the entire disclosure of which is incorporated herein by this reference.

The Kv1.3 channel is a voltage-activated potassium (K+) channel that shows a fast activation and slow C-type inactivation and recovery. The channel is encoded by KCNA3, located in humans on chromosome 1 at position 111214310-111217655 (RGD ID 1342945). While Kv1.3 channels are found in all T and B cell subsets in the resting state, their expression is markedly upregulated in activated effector memory T cells (TEMs) and Ig class-switched memory B cells from ~250 to ~1500 channels per cell. The two major K+ channels that are expressed in lymphocytes, Kv1.3 and KCa3.1, are promising targets for the treatment of autoimmune disorders, including but not limited to multiple sclerosis, type 1 diabetes, rheumatoid arthritis, psoriasis, systemic lupus erythematosus, and rapidly progressive glomerulonephritis. Moreover, KCa3.1 is related to acute immune responses and Kv1.3 is related to chronic immune responses. Combined inhibition may enhance effects in autoimmune disorders or other conditions where suppression of the immune system is desired, e.g. graft/organ rejection syndrome. In specific embodiments the siRNA is effective for inhibiting an ion selected from Kv1.3, KCa3.1 and combinations thereof. In more specific embodiments the siRNA is effective for inhibiting Kv1.3. Where a functionalized nanovesicle is encapsulated with siRNA effective for inhibiting Kv1.3, for example, it may be referred to herein as siKv1.3. Inhibition may be effectuated by complete or partial knockout (sometimes referred to as "knockdown") of KCNA3 or by knockout/knockdown of any gene necessary for the synthesis or functioning of Kv1.3.

In specific embodiments, the immune system cells are T-cells and the target subset of the T-cells is a CD45RO positive isoform of $T_M$ cells. An exemplary effective binding partner may be CD45RO antibody or any fragment thereof retaining binding efficacy for CD45RO+. In specific embodiments the antibody comprises monoclonal antibody. In very specific embodiments the T-cell comprises $T_M$.

A person of ordinary skill in the art is aware that many different siRNA may be generated for effective knockdown/knockout of a given gene, and that generation of siRNA is within the skill of the ordinary artisan. Common methods for generating siRNA effective for knockdown or knockout of a given gene include chemical synthesis, in vitro transcription, digestion of long dsRNA by an RNase III family enzyme (e.g. Dicer, RNase III), expression in cells from an siRNA expression plasmid or viral vector, and expression in cells from a PCR-derived siRNA expression cassette. Guidance is provided, for example, in Sui G, Soohoo et al. (2002) A DNA vector-based RNAi technology to suppress gene expression in mammalian cells. Proc Natl Acad Sci USA 99: 5515-20, Brummelkamp T R, et al. (2002) A system for stable expression of short interfering RNAs in mammalian cells. Science 296: 550-3, and Paul C P et al. (2002) Effective expression of small interfering RNA in human cells. Nature Biotechnology 20: 505-8, the entire disclosures of which are incorporated herein by this reference.

In specific embodiments the siRNA aspect of the compositions comprises a 19-25 nucleotide Kv1.3-specific siRNA. According to very specific embodiments, the siRNA is selected from the group consisting of GUAACUCGACUCUGAGUAAtt (SEQ ID NO: 1), UUACUCAGAGUCGAGUUACtt (SEQ ID NO: 2), CUUACCCUCUCUCUCUUAAtt (SEQ ID NO: 3, UUAAGAGAGAGAGGGUAAGtt (SEQ ID NO: 4), GAUGGACCUUUCAACGUUAtt (SEQ ID NO: 5), UAACGUUGAAAGGUCCAUCtt (SEQ ID NO: 6), and duplexes thereof.

In some embodiments, the composition is formulated for systemic administration. According to specific embodiments the composition may be formulated for parenteral administration, for example, intravenous, intra-arterial, intraosseous infusion, intracerebral, intracerebroventricular, and intrathecal administration. Lipid nanovesicles are ideal for delivery via injectable routes since they are biocompatible and solutions may be formulated surfactant-free.

Other embodiments are directed to methods of treating a patient suffering from a condition of the immune system characterized by overexpressed and/or hyperexcitable immune system cells. The methods comprising administering a composition according to aspects of the invention, formulated to selectively bind to a target subset of the immune system cells and transfect it with siRNA effective to knockdown or knockout an ion channel implicated in $Ca^{2+}$ flux. The compositions comprise: lipid nanovesicles, lipid nanovesicles functionalized with antibody selective for a membrane protein unique to the target subset. In specific embodiments the antibody comprises monoclonal antibody. The antibody is bound to a surface of the lipid nanovesicle either directly or indirectly. The nanovesicle is encapsulated with siRNA effective for inhibiting expression of an ion channel of the target subset cells upon transfection. According to specific embodiments, the immune system cell is a T-cell, the subset of the T-cell is a CD45RO+ isoform, the membrane protein is unique to the CD45RO positive isoform, and the antibody comprises anti-CD45LRO. In very specific embodiments the T-cell comprises a $T_M$ cell.

In specific method embodiments the ion channel comprises Kv1.3 and the siRNA comprise one or more of a 19-25 nucleotide Kv1.3-specific siRNA, for example, the siRNA may be selected from the group consisting of GUAACUCGACUCUGAGUAAtt (SEQ ID NO: 1), UUACUCAGAGUCGAGUUACtt (SEQ ID NO: 2), CUUACCCUCUCUCUCUUAAtt (SEQ ID NO: 3, UUAAGAGAGAGAGGGUAAGtt (SEQ ID NO: 4), GAUGGACCUUUCAACGUUAtt (SEQ ID NO: 5), UAACGUUGAAAGGUCCAUCtt (SEQ ID NO: 6), and duplexes thereof.

Although this disclosure illustrates a broad embodiment of the invention by specific example (SLE), the compositions and methods are applicable to any autoimmune disorder characterized by hyperexcited or over-expressed $T_M$ cells. Exemplary autoimmune disorders which may be effectively treated include, but are not limited to Rheumatoid arthritis, Type 1 diabetes, Multiple Sclerosis, Psoriasis, Vasculitis, Alopecia areata, Systemic Lupus Erythematosus, Polymyalgia rheumatica, Ankylosing spondylitis, Celiac disease, Sjögren's syndrome, and Temporal arteritis.

According to specific embodiments, a therapeutic regimen comprises dosing according to a schedule based on severity of the disease across a therapeutic time frame. Severity of the disease may be assessed, for example, by calculating a ratio of $T_M$ to naïve T cells in plasma of the patient sampled across the therapeutic time frame. Autoimmune disorders are generally characterized by disruption in ordinary homeostasis and an increase in the ratio. Treatment designed to effectuate a reduction in $T_M$ cells should restore a nonpathological equilibrium across the therapeutic time frame.

Embodiments providing methods of manufacturing an agent, specifically a solid lipid nanoparticle/nanovesicle, effective for the treatment of a chronic immune system disorder characterized by over-expression and/or hyperexcitability of immune system cells, are also provided. In specific embodiments the methods comprise: identifying a membrane protein substantially unique to a target subset of an immune system cell population; encapsulating siRNA effective for inhibiting an ion channel of the target subset cell into a lipid nanovesicle; and functionalizing a surface of the lipid nanovesicle with an antibody to the membrane protein.

A fundamental advantage of the instant methods relates to the selectivity for TM cells over naive T cells or other cell populations. Embodiments of the invention provide methods of treating a patient suffering from an immune system disorder characterized by hyperexcitable $T_M$ cells by selectively suppressing the function of $T_M$ cells and interrupting a CD40-CD40L pathway between B and T cells of the immune system, wherein selectively is defined as substantially avoiding altering expression of non $T_M$-cells.

The present subject matter demonstrates for the first time that gene expression of a T cell subpopulation can be manipulated by lipid-based unilamellar, antibody-functionalized NPs. The data generated for the illustrative embodiments verifies that PEG-coated lipid NPs can be rapidly functionalized with antibodies against specific T cell markers using streptavidin-biotin complex. The NPs functionalized with CD45RO antibodies selectively bind to a subtype of T cells, the CD45RO+ $T_M$'s that are key players in chronic immune disorders like autoimmunity. Data further demonstrates that $T_M$ cells bind and endocytose the NPs loaded with siRNAs. Ultimately, patch-clamp measurements demonstrate the efficient knock-down of Kv1.3, and flow cytometric $Ca^{2+}$-flux experiments show that down-regulation of Kv1.3 channels by Kv1.3-NPs inhibits $Ca^{2+}$ influx into $T_M$ cells. Since $Ca^{2+}$ influx is one of the earliest events in T cell activation, these data indicate that Kv1.3-NPs are effective immune suppressive agents that selectively reduce $T_M$ cell activation. It will be apparent to a person of ordinary skill in the art that the specific inventive nanovesicles disclosed herein may be easily modified to target other cells and/or deliver other drugs/siRNAs and may further be developed into personalized therapeutics, i.e. specifically tailored to individual patients.

The following examples are intended to illustrate particular embodiments, aspects, and features of the invention and should not be construed to limit the full scope as defined by the appended claims.

EXAMPLES

Example 1

This example demonstrates synthesis of an antibody-functionalized lipid nanovesicle according to specific embodiments of the invention.

Human T lymphocytes were isolated from the blood of healthy consented donors and discarded blood units from Hoxworth Blood Center (UC, Cincinnati) using RosetteSep™ Human Total Lymphocyte Enrichment Cocktail (StemCell Technologies). The protocol was approved by University of Cincinnati IRB. T cells were maintained in RPMI-1640 medium supplemented with 10% human serum, 200 U/ml penicillin, 200 µg/ml streptomycin and 10 mM HEPES (T cell medium). Cells were activated with 4-10 µg/ml PHA (phytohemaglutinnin-A, Sigma-Aldrich) in presence of peripheral blood mononuclear cells (PBMC) for 72 hrs.

NP Preparation

Chloroform-dissolved lipids L-α-phosphatidylcholine (PC), 1,2-distearoyl-sn-glycero-3-phosphoethanolamine-N-[biotinyl(polyethylene glycol)-2000] (PE-PEG-biotin) and cholesterol (CH) (Avanti Polar Lipids Inc.) were mixed in a 3:1:1 mole ratio, dried with $N_2$ gas, rehydrated with PBS (pH=7.4), and shaken in an incubator at 37° C. for 2 hours to make multilamellar vesicles (MLV). After sonication (Misonix, XL-2000 series), the sample was extruded with 100 nm filter to synthesize unilamellar vesicles (ULV=NP) (LIPEX™ Thermobarrel Extruder, Northern Lipids Inc.). NPs with lipid dye CellVueRed (Molecular Targeting Technologies Inc.) were prepared as described above except the lipid dye was added to the lipid mixture before drying with $N_2$.

Functionalization of NPs

Biotynilated antibodies (mouse anti-human IgG and CD45RO, 10 µg/ml, BD Biosciences) were first incubated with 10 µg/ml Alexa-647 or Alexa-488 conjugated streptavidin (SAV, Life Technologies) in PBS. Then the antibody-SAV complex was added to the 100 nm NP and incubated at room temperature. The unbound antibody and SAV was removed using CL-4B columns (GE Healthcare Life Sciences). NPs later used for siRNA encapsulation were frozen at −80° C. for 2-4 hrs, and then lyophilized for 48 hrs (Labconco, FreeZone 6 Freeze Dryer).

siRNA Encapsulation into NPs

Lyophilized CD45RO-NPs (app. 50 µg lipid) were reconstructed in 100 µl nuclease-free water containing 200-400 pmol of either Kv1.3-siRNA (Kv1.3-NPs; Santa-Cruz Biotechnology Inc.) or scramble Cy3-siRNA (Scramble-NPs Applied Biosystems) complexed with protamine-sulfate (1:5 molar ratio).

Size Measurement of NPs

Dynamic Light Scattering (DLS) and intensity fluctuation correlation methods was used to determine NPs diameter with Zetasizer Nano ZS (Malvern Instrument). ULVs were visualized using scanning electron microscopy (SEM, Hitachi SU 8000), scanning transmission electron microscopy (STEM), and WETSEM for hydrated samples. Briefly, for TEM observation, lyophilized nanoparticles were first dispersed in Methanol and lipid solution (50 µL) was dropped and dried on Cu grid (TED PELLA, G200HS). The samples were inserted and visualized in the STEM microscope at 30 kV. Also, lipid NPs were visualized in hydrated state using WETSEM™ technology (EI-Mul Technology, Israel). Liquid dish membrane (QX 102 capsule) was first coated by poly-L-lysine and suspended NPssolution (15 µL) were attached on the membrane and lipid vesicles were visualized using SEM at 25 kV.

Immunocytochemistry

T cells incubated with antibody-coated NPs were plated onto poly-L-lysine coated glass coverslips and fixed with 1% formaldehyde. When cells were labeled with mouse anti-human CD45RA-Alexa488 antibody (Biolegend) to test CD45RO-NPs specificity, blocking with 10% FCS in PBS (pH 7.4) preceded incubation with the CD45RA antibody. Coverslips were mounted onto glass slides using Fluoromount G (eBioScience).

Confocal Microscopy

Zeiss LSM 510 META was used for confocal images of the cells. The He—Ne laser was selected to excite fluorophore Alexa647 (line 633 nm) and Cy3/CellVueRed (line 543 nm), and Argon laser (line 488 nm) to visualize Alexa488. The thickness of the slices and z-stacks were set to 1 μm.

Electrophysiology

Kv1.3 currents were recorded using Axopatch 200B amplifier (Molecular Devices) in whole-cell voltage-clamp configuration. The bath solution was (in mM): 145 NaCl, 5 KCl, 1 $MgCl_2$, 2.5 $CaCl_2$, 5.5 glucose, 10 HEPES (pH 7.35). The pipette solution contained (in mM): 140 KF, 11 K2EGTA, 1 $CaCl_2$, 2 $MgCl_2$, and 10 HEPES (pH 7.22) [21]. Kv1.3 currents were evoked by 15-ms-long depolarizations to +50 mV from a holding potential (HP) of −120 mV. The amplitude of the peak current was determined at +50 mV, and the current density (CD) was given as the ratio of peak current at +50 mV and the whole-cell cell capacitance (which is a measurement of cell size/surface area). The CD is proportional to the number of Kv1.3 channels per unit area.

Cell Transfection

T cells were transected by nucleofection with Kv1.3 specific and scramble Cy3-labeld siRNAs along with pmaxGFP using 4D-Nucleofector System according to the manufacturer's protocol (Lonza Group Ltd.) The cells were studied 24 hours post transfection.

Treatment of T Cells with siRNA-Encapsulated NPs (siRNA-NPs)

$3\times10^5$ T cells (either activated, for electrophysiological experiments, or resting, for $Ca^{2+}$ measurements) in T cell medium were mixed with 50 μl of siRNA-NPs, and incubated for 24 h in cell culture incubator (37° C., 5% $CO_2$, humidified).

$Ca^{2+}$ Measurement $Ca^{2+}$ was measured using the $Ca^{2+}$ add-back method as described by Baba et al. Briefly, $1\times10^6$ CD3+ cells were loaded with 1:1000 fold of 2 mg/ml Indo-1/AM ratiometric dye and 0.015% Pluronic 127 (Life Technologies, Carlsbad, Calif.) in Hank's balanced salt solution containing 1 mM $CaCl_2$, 1 mM $MgCl_2$ and 1% FCS for 30 min at 37° C., then washed three times in Hank's balanced salt solution supplemented with 10 mM HEPES (pH 7.0) and 1% FCS. Prior to measurements, cells were resuspended in a calcium-depleted solution prepared from the Hank's balanced salt solution/HEPES solution mentioned above and supplemented with 0.5 mM EGTA (pH 7.4). Samples were kept at 37° C. until analysis. Indo-1 fluorescence ratio (indicative of the $[Ca^{2+}]i$) in T cells were measured by flow cytometry on an LSRII flow cytometer (Beckton Dickinson) using a 20 mW UV (355 nm) laser and capturing fluorescence using 505 nm long pass and 530/30 band pass filters for unbound Indo-1 and a 405/20 band pass filter for $Ca^{2+}$-bound Indo-1. Changes in Indo-1 fluorescence ratio were measured in $T_M$ cells by gating on CD45RO-NPs labeled with SAV-Alexa488.

The following protocol was implemented. Cells were exposed to thapsigargin (TG, 1 μM) in 0 mM $Ca^{2+}$ solution followed by the 2 mM $Ca^{2+}$-containing solution. This protocol allows measuring $Ca^{2+}$ influx, which originates exclusively through CRAC channels. Exposure of the cells to TG leads to depletion of intracellular $Ca^{2+}$ stores and activation of the signaling steps necessary for opening of CRAC channels. Ca2+ influx through the opened CRAC channels is then induced by increasing the extracellular $Ca^{2+}$ concentration ($[Ca^{2+}]$). Samples were recorded at 300 events/second on a 'low' flow rate. Analysis of the kinetics was performed using Flow-Jo software (Tree Star Inc).

Area under the curve (AUC) was calculated for that part of $Ca^{2+}$-response curve when cells were bathed in 2 mM $Ca^{2+}$ solution after TG addition, and it estimates the average $Ca^{2+}$ influx into the cell. $Ca^{2+}$ amplitudes ($\Delta Ca^{2+}$) was given as the peak intensity ratio of Indo-1 upon addition of 2 mM Ca2+ corrected with the mean Indo-1 ratio at 0 mM Ca2+ before TG addition (baseline was subtracted from the peak value).

All reagents were purchased from Sigma-Aldrich Ltd., if not otherwise stated. ShK was bought from Bachem Holding AG. Statistical comparison was performed using Student's t-test; the significance level was set to 0.05. The values are given as mean±SEM.

Results

CD45RO-NPs Specifically Bind to and are Internalized by $T_M$ Cells.

In cell-targeted therapy it is critical to design NPs which can attach with their cargo only to the selected cells/tissues. Hence, whether CD45RO-NPs were able to bind selectively to $T_M$ cells was confirmed by the following procedure. Primary human T cells were exposed to fluorescent (SAV conjugated with Alexa647, blue) lyophilized/reconstructed CD45RO-NPs or IgG-NPs. After 24 hr incubation (at 37° C. in the presence of 10% human serum), the cells were fixed, and naïve T cells were labeled with Alexa488 conjugated CD45RA antibody (FIG. 2B). Confocal micrographs demonstrated that CD45RO-NPs bound only to $T_M$ but not naïve T cells. The merged images showed clearly that the cells, which were decorated with CD45RO-NPs, do not express CD45RA. To show the lack of CD45RO-NP non-specific binding, T cells were incubated with IgG-NPs. Confocal images illustrated that IgG-NPs did not adhere to the membrane of T cells.

CD45RO-NPs Specifically Bind to CD45RO+ $T_M$ Cells

Figure 6:
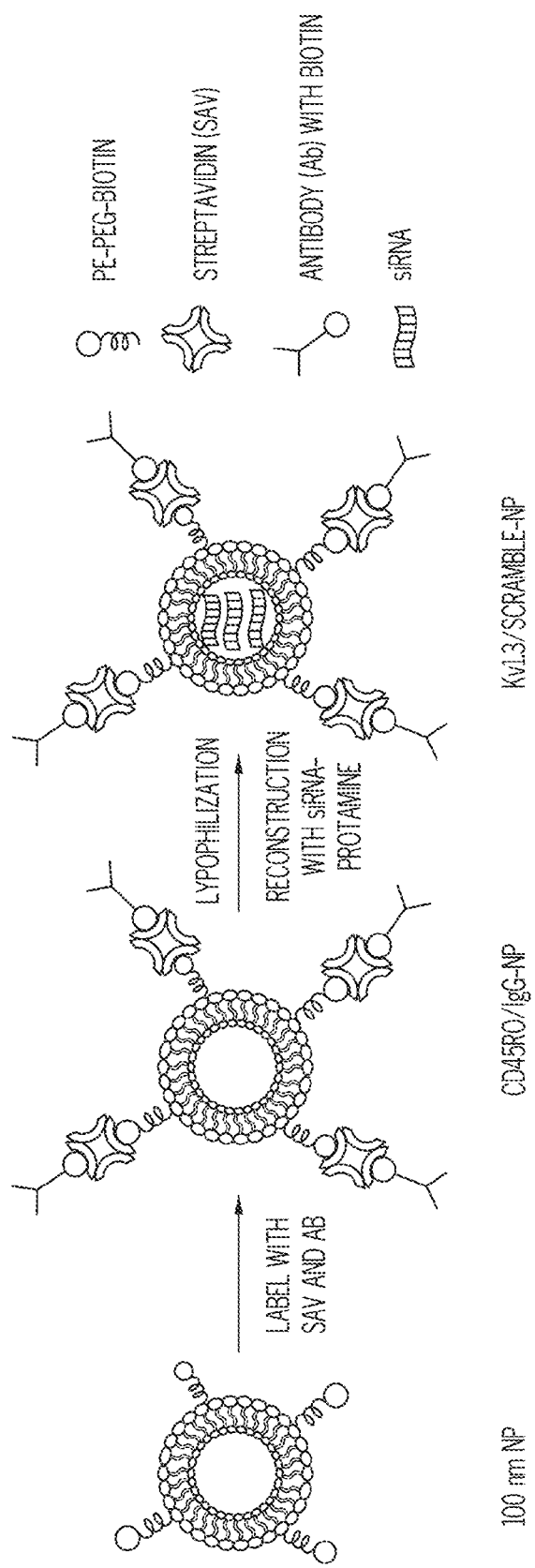
FIG. 6. Drawing illustrating functionalization of a lipid NP and incorporation of Kv1.3 SiRNA (siKv1.3).

Further experiments showed that bound CD45RO-NPs were internalized by $T_M$ cells (FIG. 6). CD45RO-NPs labeled with CellVueRed lipid dye and SAV-Alexa647 were utilized. After a 24-hour-incubation of T cells with these NPs, cells were plated and the CD45RO antibodies on the NPs, which had already interacted with the cells, were labeled with Alexa488 secondary antibody. Since this latter step occurs in non-permeabilized cells, this intervention allows exclusive staining of the CD45RO-NPs attached to the cell membrane. Therefore, the merge image demonstrated internalization of NPs by purple fluorescence, as well as their fusion to the plasma membrane (white and yellow fluorescence). Similar distribution was observed with CD45RO-NPs that underwent lyophilization indicating that this procedure did not compromise the antibody binding, i.e. the antibodies remained attached to the surface of the NPs. As shown before, the fluorescence signals of SAV-Alexa647 and CellVueRed of the NPs were co-localized only in a subset of T cells. Overall these experimental results confirm that lyophilized CD45RO-NPs can selectively target and accumulate in/on $T_M$ cells. Hence, CD45RO-NPs represent a suitable carrier for siRNA delivery and gene knock-down in $T_M$'s.

$T_M$ Cells Endocytose CD45RO-NPs; Kv1.3 siRNA Delivery to $T_M$ Cells

Even though the CD45RO-NPs recognize, bind to and enter the $T_M$'s, this does not automatically mean that the encapsulated cargo is released into the cytosol. Consequently, in the next step CD45RO-NPs loaded with a Cy3-labeled scramble siRNA to visualize whether these NPs are able to deliver siRNAs into $T_M$ cells were utilized. As detailed above, freeze-dried CD45RO-NPs were reconstructed in protamine-complexed control Cy3-siRNA-containing water and added to primary T cell for 24 hrs. CD45RO-NPs (SAV-Alexa647, blue) loaded with Cy3- siRNA (red) were capable of attaching to TM cells selectively, and the siRNAs were detected intracellularly in CD45RO+ cells that picked up the CD45RO-NPs (merged image). A further confirmation of specific NP-assisted siRNA delivery was shown in confocal snapshots of T cells treated with naked Cy3-siRNA/protamine solution for 24 hr. No intracellular red fluorescence of Cy3-siRNA was detected. Overall, these findings show that CD45RO-NPs are able to serve as transporters of siRNAs into the $T_M$'s.

Cy3-siRNA Uptake of $T_M$ Cells; Kv1.3-NPs Reduce Expression of Kv1.3 Channels

To measure the efficacy of Kv1.3 channels' knock-down by Kv1.3-NPs, a single cell technique—patch-clamping—was applied to compare the currents through Kv1.3 channels in Kv1.3-NPs (Kv1.3 siRNA loaded CD45RO-NPs) and Scramble-NPs (control siRNA encapsulated CD45RO-NPs) treated cells. These measurements allow estimation of the expression of functional Kv1.3 channels in single TM cells. In these experiments, the Alexa488 fluorophore conjugated SAV moiety of the NPs was used to visualize the cells that have bound/incorporated the NPs. Only cells that displayed green fluorescence were selected for electrophysiological recording. The knock-down efficiency of Kv1.3-NPs was compared with that of naked (non NP encapsulated/transfected; see materials and methods) Kv1.3 siRNAs. These Kv1.3 siRNAs were shown to be effective inhibitors of Kv1.3 expression. Activated T cells were co-transfected with naked Kv1.3 or scramble siRNAs and a GFP-encoding plasmid (moles of siRNA far exceeded that of the pMaxGFP vector). GFP-expressing cells were selected to undergo patch-clamping as they also contained siRNAs. Whole-cell Kv1.3 current traces in T cells treated with Scramble-NPs and Kv1.3-NPs were recorded. The Kv1.3 current was significantly lower in the cells treated with Kv1.3-NPs than in Scramble-NPs' treated cells. The extent of the decrease in Kv1.3 peak current and CD was app. 60% (3 donors for each experiment, n≥15 cells) in Kv1.3-NP treated cells and Kv1.3-siRNA transfected cells. These data prove that Kv1.3 siRNAs delivered by CD45RO-NPs effectively down-regulated the expression of Kv1.3 channels in $T_M$ cells.

CD45RO-Kv1.3NPs Down-Regulate Kv1.3 Expression in $T_M$ Cells; $Ca^{2+}$-Signaling in Memory T Cells was Reduced by Kv1.3-NP Gene Knock-Down Kv1.3 channels play an important role in the regulation of $Ca^{2+}$ signaling in $T_M$ cells, and the inhibition of these channels reduces the influx of $Ca^{2+}$ through the CRAC channels. Hence, the $Ca^{2+}$-response of T cells treated with siRNA-loaded CD45RO-NPs was studied. In this set of experiments, resting T cells were incubated with either Kv1.3-NPs or Scramble-NPs. Cells treated with empty CD45RO-NPs or nothing served as further controls. Twenty-four hours after treatment, $Ca^{2+}$ measurements were performed. These were performed by flow cytometry, which allows gating on $T_M$ cells. Indo1-loaded T cells were kept in $Ca^{2+}$-free extracellular solution. Addition of TG (1 μM) induced a small increase in the $[Ca^{2+}]i$ (measured as an increase in the fluorescence ratio of Indo-1), which corresponds to the emptying of intracellular $Ca^{2+}$ store (ER, endoplasmic reticulum). This intervention is used to artificially open the CRAC channels because it activates a $Ca^{2+}$ sensor in the ER, which moves in proximity and opens the pore forming subunit of the CRAC channel in the plasma membrane. Yet, no further $[Ca^{2+}]i$ increase is observed because the external solution contains no $Ca^{2+}$. At this point the external solution was changed to one containing 2 mM $Ca^{2+}$. Immediately upon increasing the extracellular $Ca^{2+}$, $Ca^{2+}$ influx through CRAC channels can be detected. This is depicted by the robust increase in $[Ca^{2+}]i$, which is monitored via the increase of the fluorescence ratio of Indo-1 at 400 and 475 nm. To validate flow-cytometric $Ca^{2+}$ measurements and confirm the role of Kv1.3 in $Ca^{2+}$-response 10 nM ShK, a Kv1.3 antagonist, was applied. Silencing the Kv1.3 gene by Kv1.3-NPs resulted in a remarkable decrease in $Ca^{2+}$ influx as compared to Scramble-NPs' treated cells. The effect of Kv1.3-NPs on $Ca^{2+}$ uptake through CRAC channels was quantified by calculating the ratio of the area under curve (AUC) and $Ca^{2+}$ peak amplitudes (ΔCa2+) for Kv1.3-silenced and control cells. Both parameters of $Ca^{2+}$ signaling decreased significantly upon Kv1.3-NP treatment of $T_M$'s (3 donors). Comparable baseline and peak $[Ca^{2+}]i$ in untreated cells, and cells treated with empty CD45RO-NPs and Scramble-NPs are indicative of a lack of effect of CD45RO antibody on $Ca^{2+}$ fluxes. These data indicate that Kv1.3 silencing with Kv1.3-NPs impairs $Ca^{2+}$ response in $T_M$ cells and Kv1.3-NPs are an effective alternative to Kv1.3 pharmacological blockers.

Figure 22A:
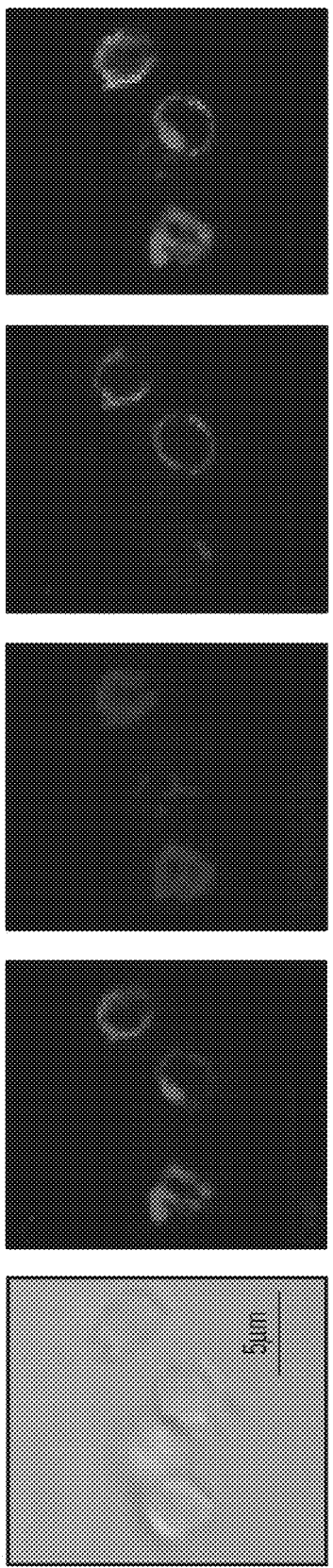
FIG. 22A. Series of confocal images of T cells incubated with CellVueRed-containing CD45RO-NPs, wherein the CD45RO antibody on the NPs was labeled with Alexa488 secondary mouse antibody (ALexa488-IgG, green) and from left to right depicting a brightfield image of the cells, CellVueRed signal of NPs, Alexa647 fluorescence of SAV, (ULVs attached $T_M$ cells), Alexa-488 fluorescence of 2nd antibody, and a merger of the red, blue and green channels; 22B) series of confocal images of T-Cells treated with lyophilized (24 hr culturing), CellVueRed-labeled CD45RO-NPs depicting from left to right, a brightfield image of the cells, a CellVueRed signal of ULVs (red); image, an Alexa-647 fluorescence image, and a merger of the red and blue channels.
Figure 22B:
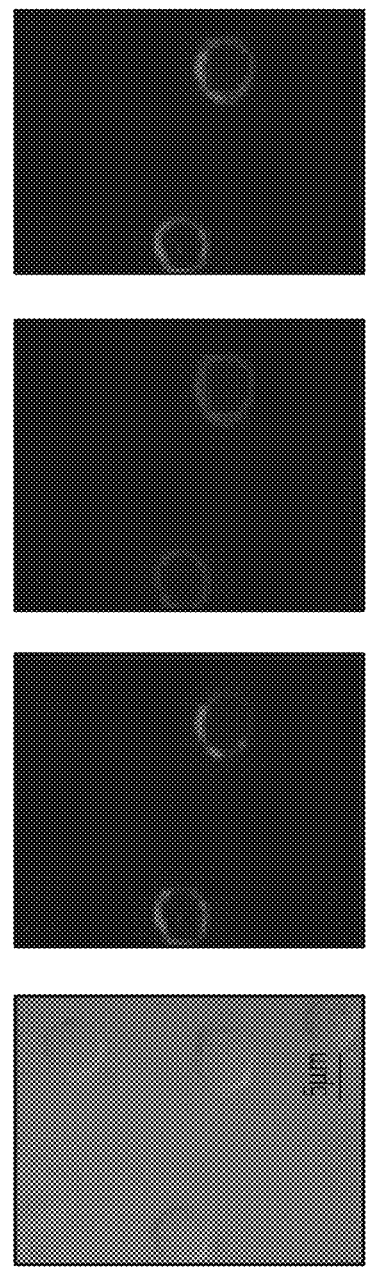
Figure 23:
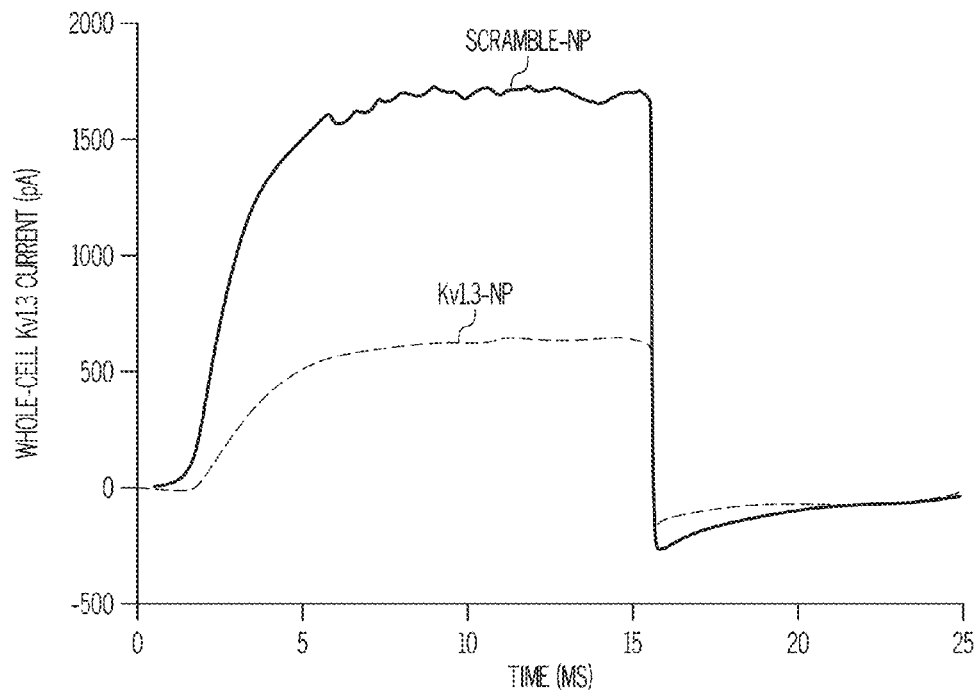
FIG. 23. Graphical representation of data showing typical whole-cell current traces of Kv1.3 channels in an activated T cell treated with either Scramble-NPs or Kv1.3-NPs. Cells were held at –120 mV and depolarized to +50 mV for 15 ms; P/5 online leak subtraction was applied.
Figure 24:
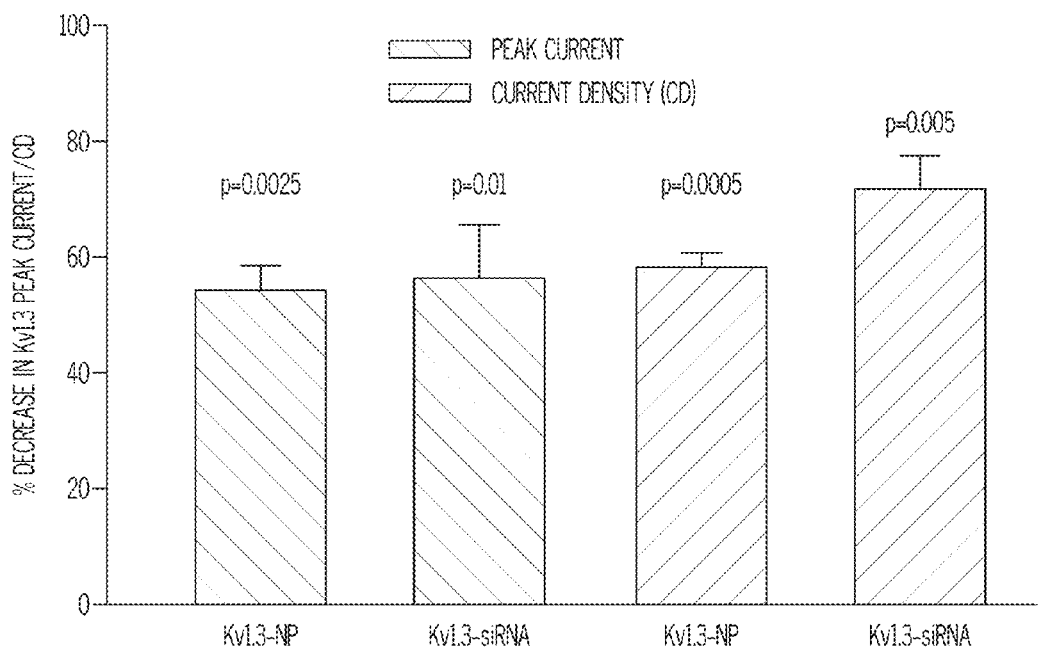
FIG. 24. Reduction of Kv1.3 expression in percentages is shown in T cells treated with Kv1.3-NPs as compared to cells incubated with Scramble-NPs (3 donors, n=18). The reduction was determined for each donor and average percent decrease for three donors is indicated (mean±SEM). The percent decrease in Kv1.3 current is also shown when T cells were transfected with specific Kv1.3 (Kv1.3-siRNA bars) and control siRNAs (3 donors, n=15).
Figure 25:
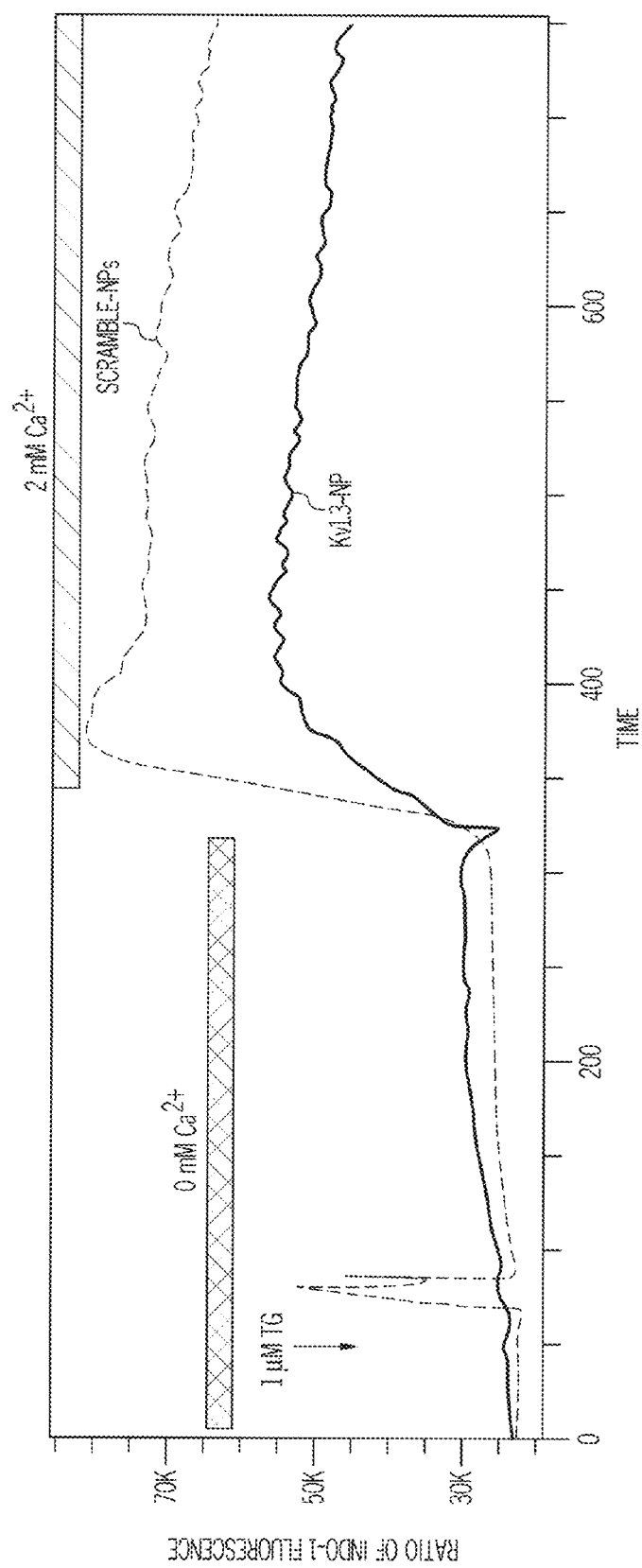
FIG. 25. Sets forth empirical evidence that Kv1.3 silencing with Kv1.3-NPs impairs $Ca^{2+}$ response in $T_M$ cells by depicting a time-course of TG-induced $Ca^{2+}$ influx through CRAC channels in resting T cells preincubated (24 h) with Kv1.3-NPs (black line) or Scramble-NPs (gray line). Fluorescence intensity of Indo-1 loaded cells was detected with flow cytometer only in Alexa-488 gated subpopulation (NPs were functionalized with SAV-Alexa488).
Figure 26:
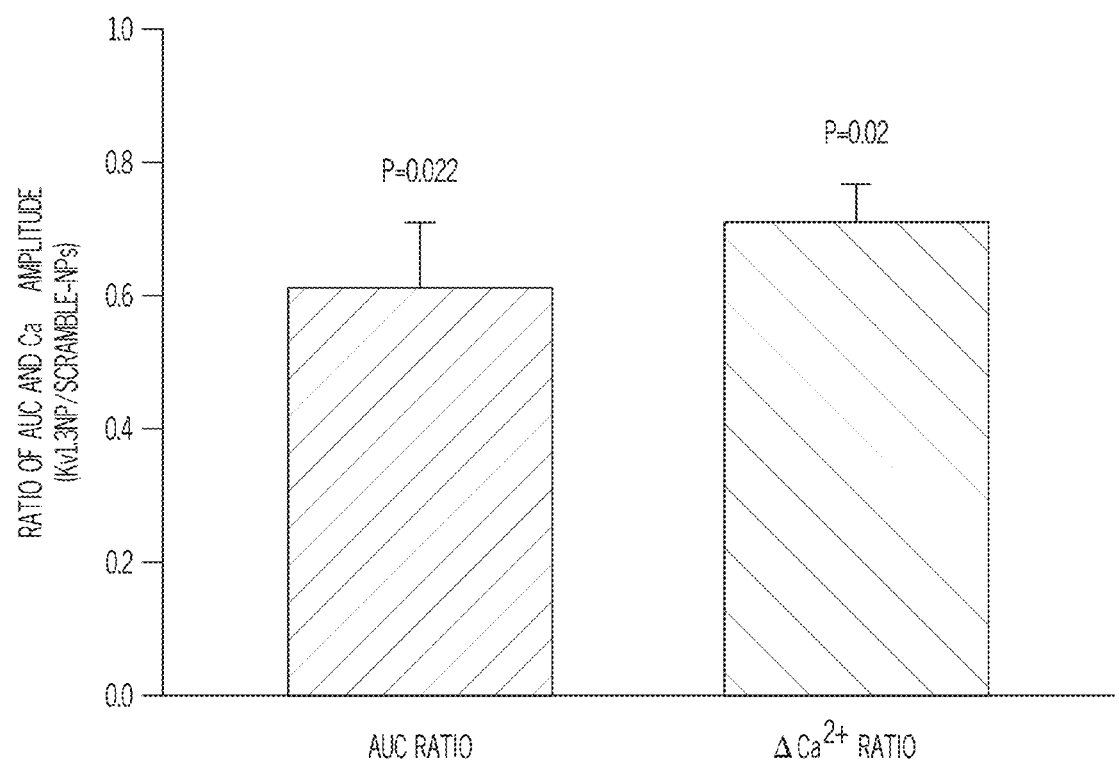
FIG. 26. Bar graph comparing ratio of AUC (area under the curve) and $Ca^{2+}$ amplitude ($\Delta Ca^{2+}$) for Kv1.3-NP and Scramble-NP treated cells (n=3 donors).

The foregoing illustrates successful synthesis and specific targeting of $T_M$ cells by anti-CD45RO-NPs. Successful transfection is highly dependent on the freeze-drying procedure involved in fabrication, needed to include siRNA into the NPs, during which the detachment of functionalizing antibodies can occur due to the non-covalent, biotin-streptavidin linkage. This could give rise to the non-selective attachment of NPs to naïve T cells (bare NPs) or simply binding of CD45RO-fluorophore-conjugated-SAV complex to the $T_M$'s. In the images set forth in FIGS. 22A and 22B, only SAV-fluorophore "positive" T cells are coated by CellVueRed-containing, CD45RO-NPs. These lipid dye labeled CD45RO-NPs can be stained with secondary antibodies when they are linked to the cell surface of TM's. Thus, stable and effective NPs were produced. The efficiency of the CD45RO-NPs was confirmed by confocal micrographs showing the cytosolic accumulation of Cy3-conjugated control siRNAs (not shown) and functional studies (FIGS. 23, 24 and 25). Patch-clamp experiments verified that Kv1.3-NPs were able to suppress Kv1.3 current/expression in TM cells. The 60% knock-down efficiency is a result of the efficacy of the siRNAs and not the amount of siRNAs in the NPs taken up by the cells since transfection of T cells with naked, specific siRNAs also had the same reduction in the Kv1.3 peak current. Further flow-cytometric $Ca^{2+}$ measurements also underline that Kv1.3-siRNA was effectively delivered into the cells by CD45RO-NPs and could reduce the number of Kv1.3 channels in TM cells: the Kv1.3-regulated $Ca^{2+}$ influx of T cells was significantly decreased (FIG. 26).

Example 2

This example illustrates application of embodiments of the inventive methods and compositions to a specific autoimmune disorder illustrated by SLE. Details of experimental protocol are similar to those provided in Example 1.

Figure 5:
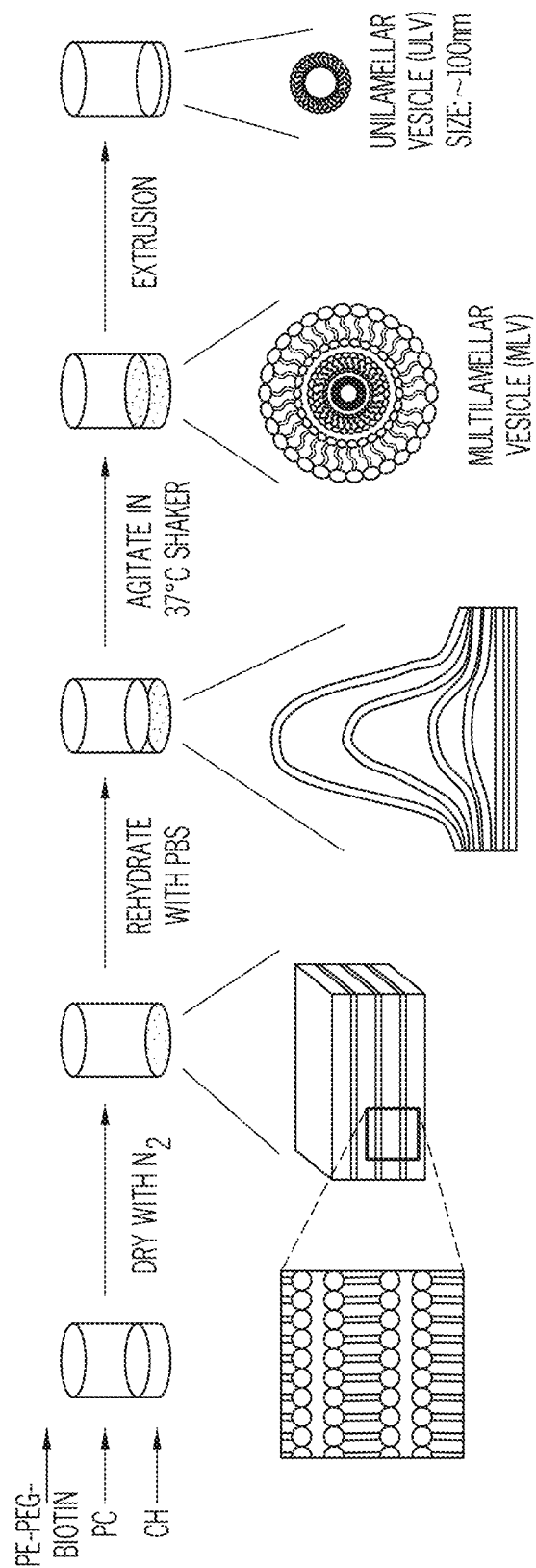
FIG. 5. Drawing illustrating basic synthetic protocol for preparation of lipid nanovesicle (NP) according to certain aspects of the invention.

CD3+ T or CD4+$T_M$ cells were isolated from whole blood of either healthy donors or SLE patients by negative selection using EasySep Magnetic Separation kit. As illustrated schematically in FIG. 5 and FIG. 6, unilamellar lipid vesicles (100 nm diameter) composed of L-α-phosphatidylcholine (PC), 1,2-distearoyl-sn-glycero-3-phosphoethanolamine-N-[biotinyl(polyethylene glycol)-2000] (PE-PEG-biotin) and cholesterol (CH) were prepared and functionalized with streptavidin and biotinylated anti-CD45RO antibody. SiRNAs directed towards Kv1.3 channels or scrambled sequence RNA were then incorporated in the vesicles. The donor cells were incubated with the NPs overnight, activated with TG, and then subjected to antibody staining and flow cytometry as described above.

Results.

i) KV1.3-NPs decrease NFAT nuclear translocation in $T_M$.

Figure 7:
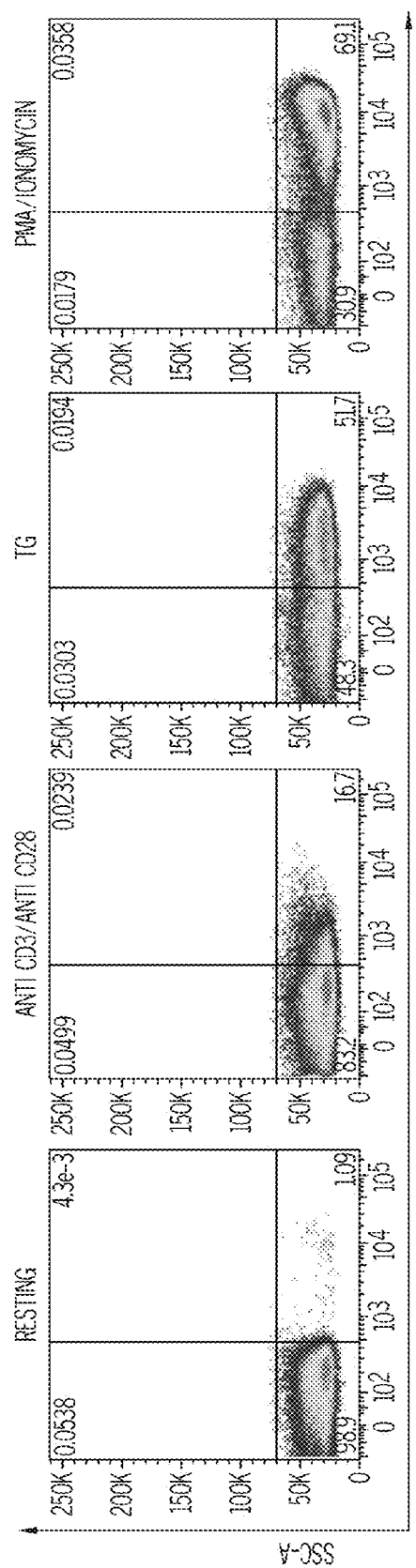
FIG. 7. Results of flow cytometry analysis of CD40L expression in CD3+ T cells that were resting or activated for 3 h with either anti-CD3/anti-CD28 antibodies, TG or PMA/Ionomycin, set forth graphically, showing that T-cell activation increases CD40L levels.
Figure 9:
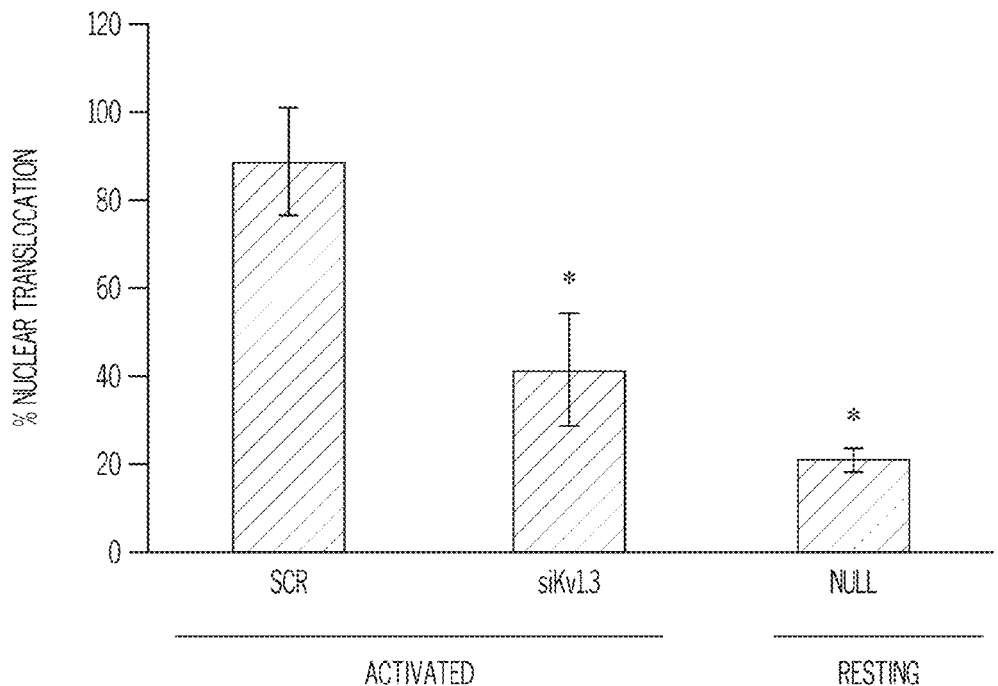
FIG. 9. Bar graph showing percentage of cells showing nuclear translocation of NFAT in 3 healthy donors.
Figure 10:
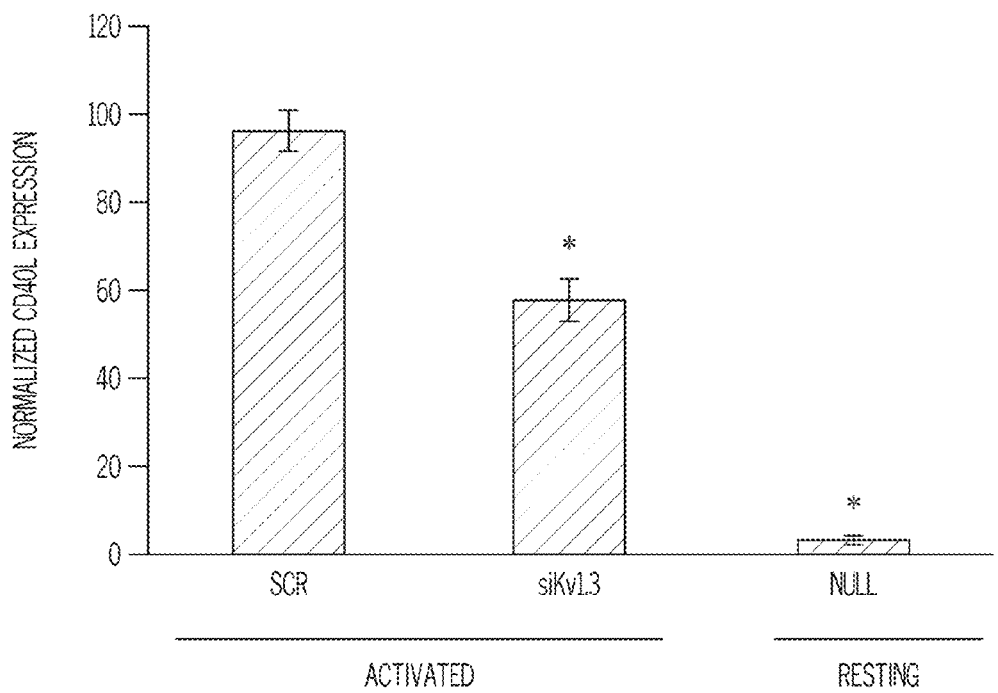
FIG. 10. CD40L expression in CD45RO+ activated T cells from 3 healthy donors transduced with NPs. Note: data are normalized to activated null-NPs. *$p<0.05$ FIG. 11. Graph showing effect of Kv1.3-NPs in SLE T-cells; CD3 cells were isolated from a SLE patient and treated with either fluorescently labeled Kv1.3-NPs or scr-NPs for 24 h. $Ca^{2+}$ influx was induced by TG for 3 h. Resting T-cells (no TG treatment, no intracellular $Ca^{2+}$ influx) transduced with scr-NPs were used as controls (middle/gray), cells were stained with anti-CD40L antibody analyzed by flow cytometry. Only cells expressing the fluorescent NPs were gated for analysis.

It is known that T cell activation increases CD40L levels. FIG. 7 sets forth results of a flow cytometry analysis of CD40L expression in CD3$^+$ T cells that were resting or activated for 3 h with either anti-CD3/anti-CD28 antibodies, TG or PMA/Ionomycin. CD3 cells were treated with fluorescently labeled Kv1.3-NPs or NPs loaded with scramble RNA (scr-NP) for 24 h. Ca$^{2+}$ influx was induced with thapsigargin (TG, which facilitates the release of Ca$^{2+}$ from intracellular stores and opens Ca$^{2+}$ channels) for 1 h. Resting T cells (no TG treatment) transduced with scr-NPs were used as controls. Cells were fixed and stained with anti-NFAT antibody and DAPI (nuclear stain). Images were acquired on the Image Stream imaging flow cytometer (Amnis, EMD Millipore). Nuclear translocation of NFAT was quantitated using the IDEAS software (Amnis, EMD Millipore) by gating on cells that had incorporated the NPs. FIGS. 8A, 8B and 8C set forth representative images of cells acquired by imaging flow cytometry showing nuclear translocation of NFAT in activated CD3 T cells and the absence of nuclear translocation in resting T cells. In particular, FIG. 8A shows representative flow cytometry images for activated T cells after treatment with scr-NPs and (FIG. 8B) siKv1.3-NPs. and FIG. 8C shows representative images for resting T cells treated with null-NPs and stained with NFAT (green-gray scale) and DAP1 (yellow-gray scale). The nuclear translocation of NFAT is indicated by the colocalization of red and green channels in the merged images. FIG. 9 shows the percentage nuclear translocation of NFAT in activated T cells treated with scr-NPs or Kv1.3-NPs, or resting T cells treated with scr-NPs, and FIG. 10 shows CD40L expression in CD45RO$^+$ activated T cells from 3 healthy donors transduced with NPs. Data show mean±SEM for 3 independent healthy donors, with 2300-3500 cells recorded per donor. Data are normalized to activated null-NPs. *p<0.05.

ii) KV1.3-NPs decrease CD40L expression in $T_M$ cells from SLE patients.

Figure 11:
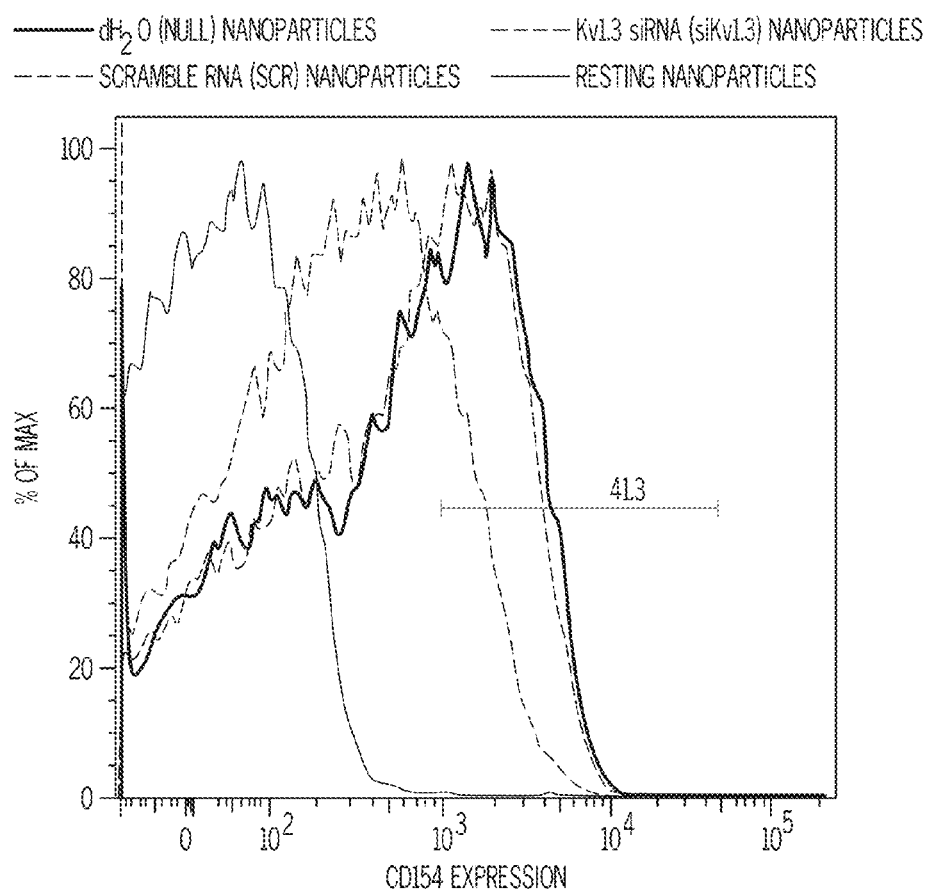
Figure 12:
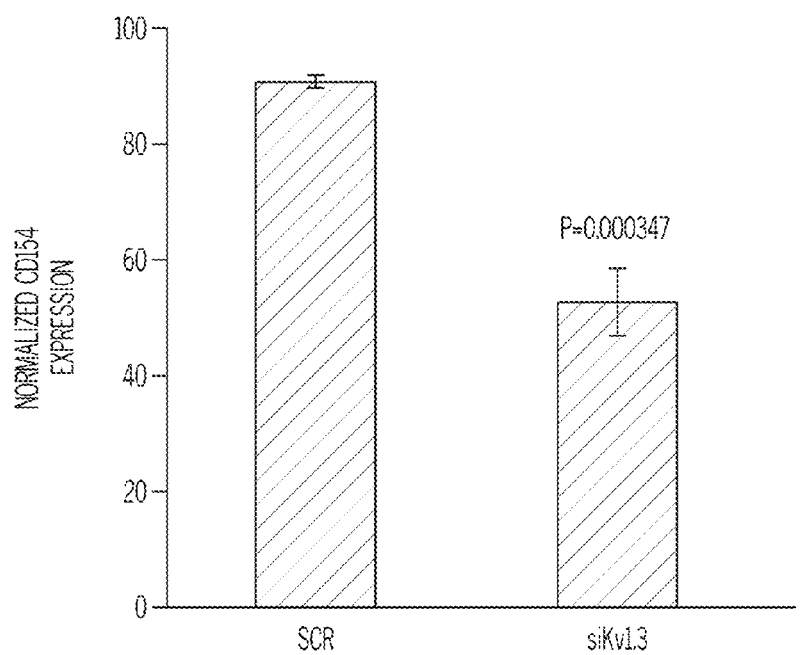
FIG. 12. Bar graph comparing the SCR and siKv1.3 data derived from graph shown in FIG. 11.
Figure 13:
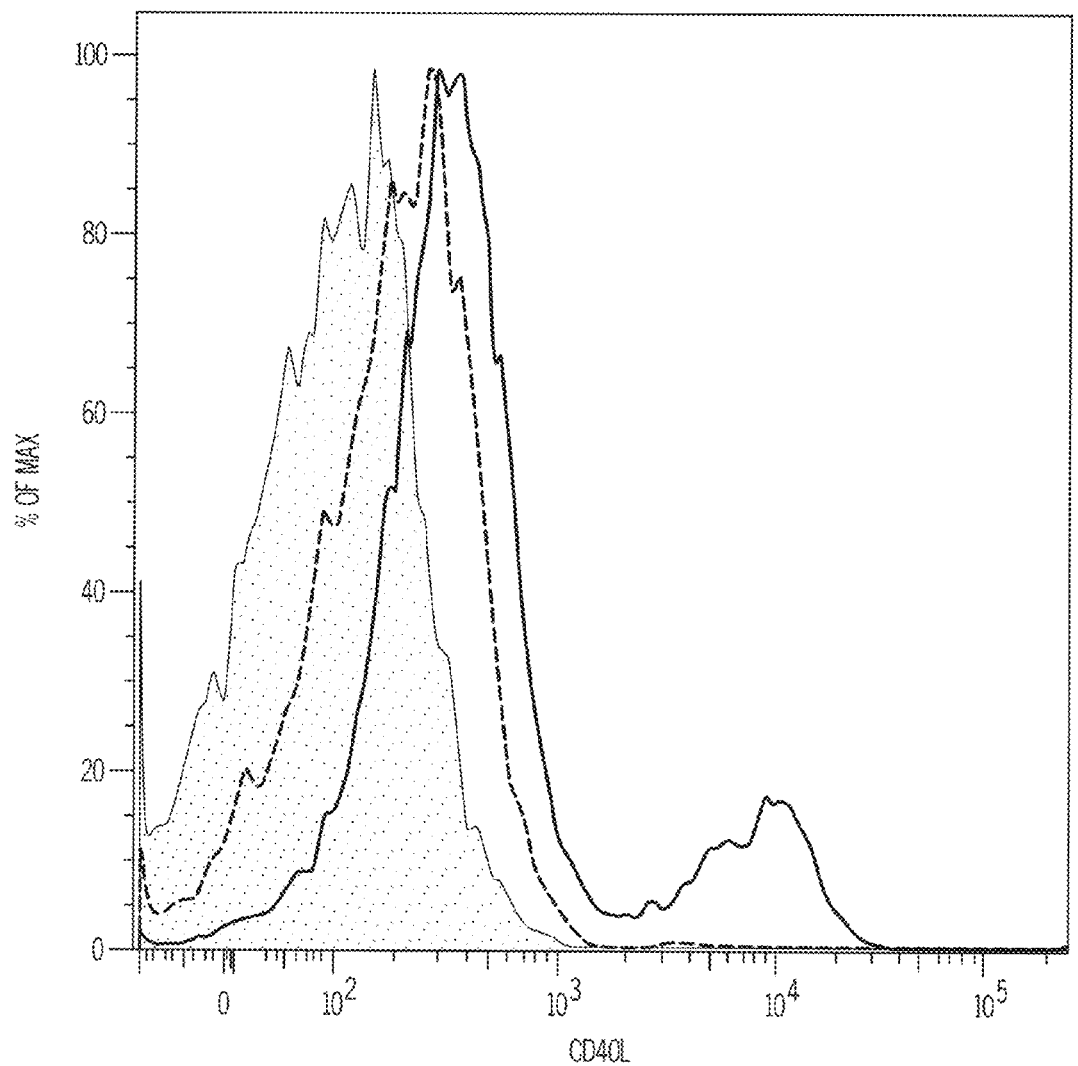
FIG. 13. Graphical depiction of CD40L expression in activated cells treated with Kv1.3-NPs, scr-NPs and null-NPs and resting cells containing scr-NPs, showing that Kv1.3-NPs reduce CD40L expression in SLE $T_M$ cells.

FIGS. 11 and 12 set forth results from the following protocol: CD3 cells were isolated from healthy donors and treated with either fluorescently labeled Kv1.3-NPs or scr-NPs or NPs without siRNA (null) for 24 h. Ca$^{2+}$ influx was induced by TG for 3 h. Resting T cells (No TG treatment, no intracellular Ca$^{2+}$ influx) transduced with scr-NPs were used as controls. Cells were stained with anti-CD40L antibody and analyzed by flow cytometry. Only cells expressing the fluorescent NPs were gated for analysis. FIG. 13 is a graphical representations showing CD40L expression in activated cells treated with Kv1.3-NPs, scr-NPs and null-NPs and resting cells containing scr-NPs. Data are normalized to null-NPs. Data show mean±SEM for 3 independent healthy donors, with 50,000 total cells recorded in each experiment.

Figure 14:
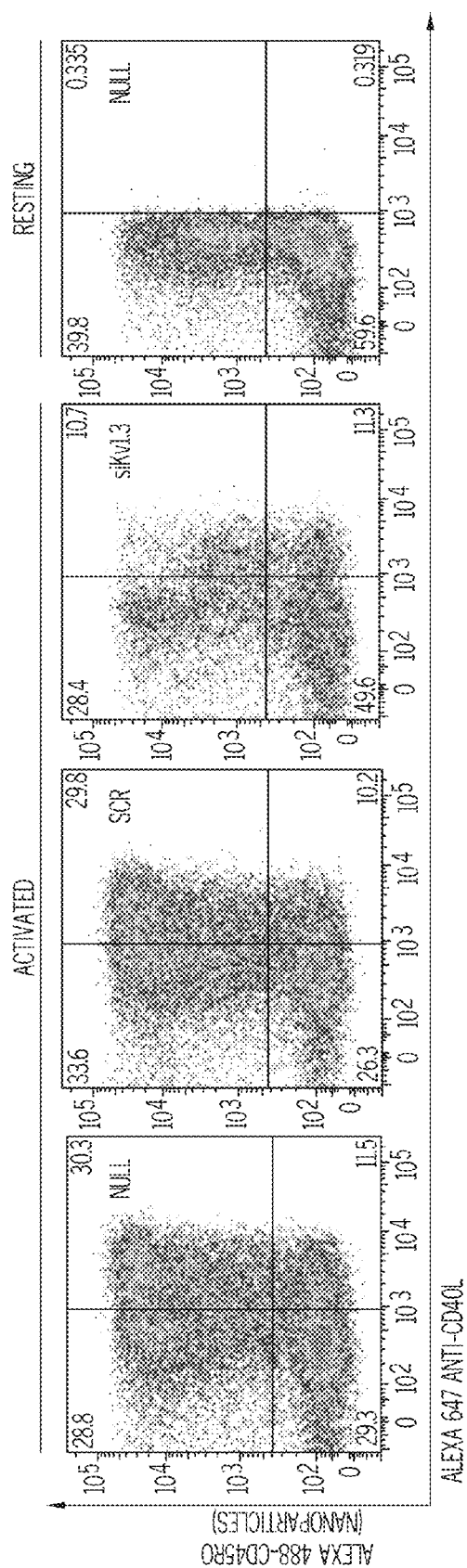
FIG. 14. Graphical representation of empirical data showing that Kv1.3-NPs decrease CD40L expression in $T_M$ cells derived from SLE patients. (A) Flow cytometry analysis of CD45RO and CD40L expression in CD3+ cells from an SLE patient treated with siKv.3-NPs, scr-NPs or neither (null-NPs) coated with Alexa488-anti-CD45RO antibody and activated with TG. Testing T cells with null-NP's were used as controls.
Figure 15A:
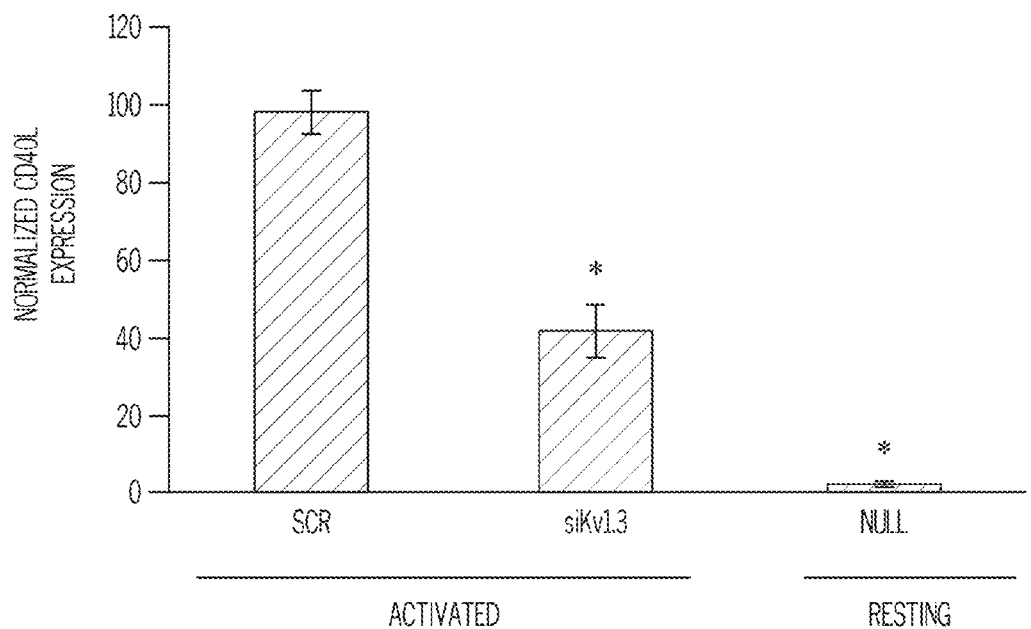
FIG. 15A. Bar graph depiction of average CD40L expression in CD45RO+ activated T cells from 3 SLE patients tranduced with NPs with data normalized to activated null-NPs; 15B) Bar graph depiction of average CD40L expression in CD45RO− activated T cells from 3 SLE patients tranduced with NPs with data normalized to activated null-NPs.
Figure 15B:
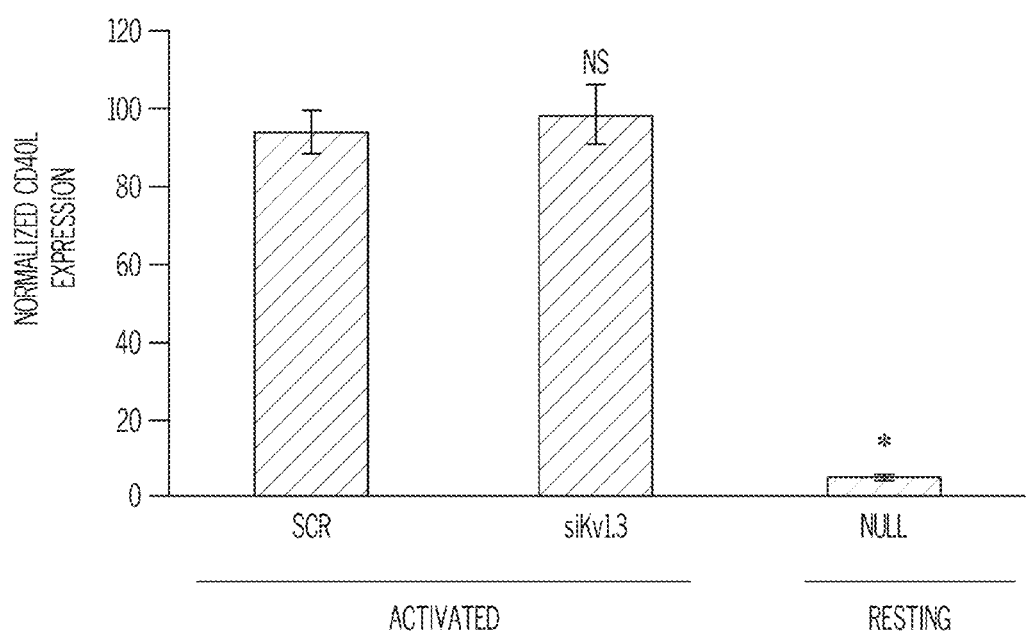
Figure 16:
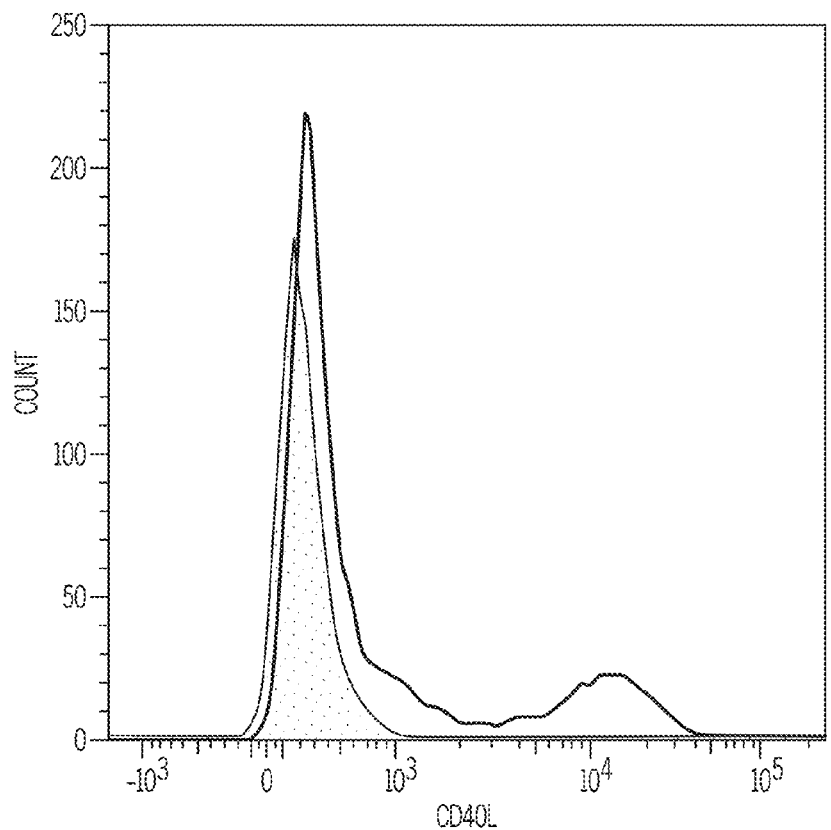
FIG. 16. Histogram of CD40L expression in activated CD45RO+ CD3+ cells from one SLE patient treated with either scr-NP or siKv1.3-NPs.
Figure 17:
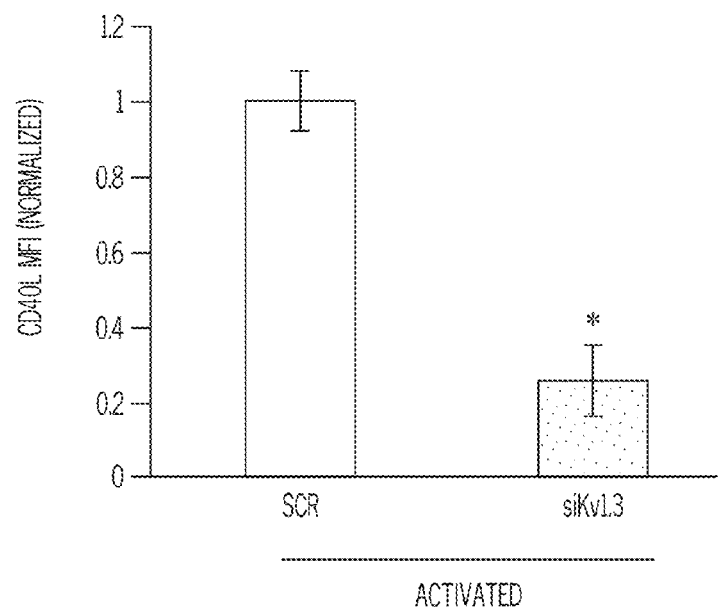
FIG. 17. Bar graph depiction of average mean fluorescence intensity (MFI) of CD40L expression in activated CD45RO+ CD3+ cells from 3 SLE patients transduced with scr-NPs or siKv1.3-NPs with data normalized to MFI of scr-NPs.

FIG. 14 sets forth a flow cytometry analysis of CD45RO and CD40L expression in CD3$^+$ T cells from an SLE patient treated with siKv1.3-NPs, scr-NPs and neither (null-NPs). NPs were coated with Alea488-anti-CD45RO antibodies and activated with TG. The resting T cells with null-NPs were used as controls. Average CD40L expression in CD45RO$^+$ or CD45RO$^-$-activated T cells from 3 SLE patients transduced with NPs are set forth graphically in FIGS. 15A and 15B. Data are normalized to activated null-NPs. FIG. 16 is a histogram of CD40L expression in activated CD45RO$^+$ CD3$^+$ cells from one SLE patient treated with either scr-NP or siKv1.3-NPs. FIG. 17 represents the average mean fluorescence intensity (MFI) of CD40L expression in activated CD45RO$^+$ CD3$^+$ cells from SLE patients transduced with scr-NPs or siKv1.3-NPs (data normalized to MFI of scr-NPs).

iii) Kv1.3-NPs induce loss of CD45RO expression in SLE T cells

Figure 18:
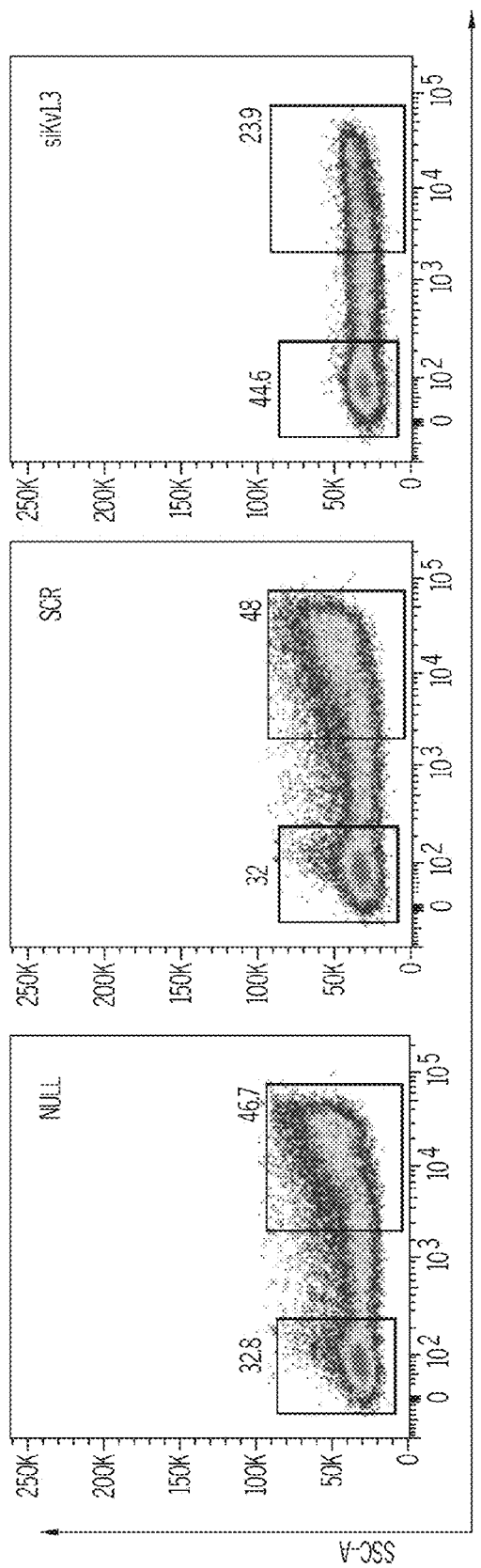
FIG. 18. Representation of data demonstrating that Kv1.3-NPs induce loss of CD45RO expression in SLE T cells; (A) Flow cytometry experiments for CD45RO expression in CD3+ cells isolated from one SLE patient incubated with null, scr or siKv1.3-NPs and then activated with TG. $T_M$ (CD45RO+) and CD45RO– populations were identified by drawing rectangle gates.
Figure 19:
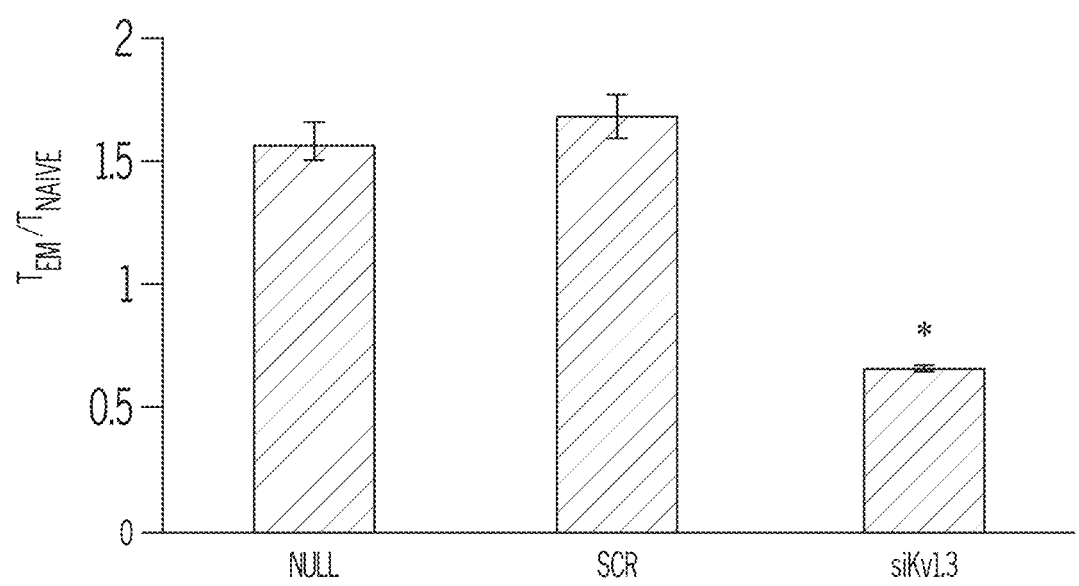
FIG. 19. Bar graph depiction of ratio of CD45RO+/CD45RO– in activated CD3 cells isolated from 3 SLE patients.
Figure 20:
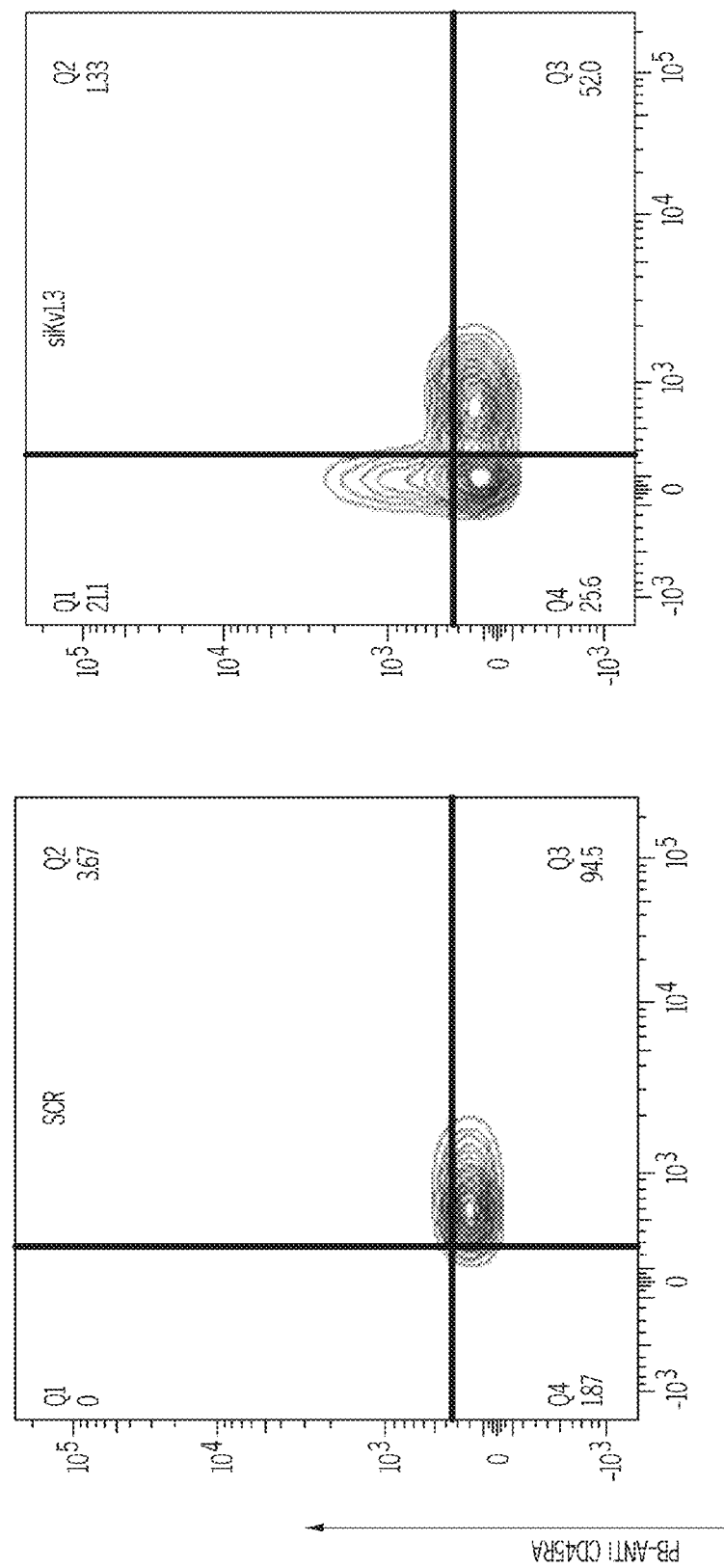
FIG. 20. Graphical representation of data demonstrating that Kv1.3-NPs decrease CD45RO expression in CD4+$T_M$ cells and switch the cell phenotype from CD45RA– to CD45RA+ from cytometry experiments for CD45RO and CD45RA expression in CD4+$T_M$ cells isolated from a healthy donor and incubated with either scr- or siKv1.3-NPs and then activated with TG.
Figure 21:
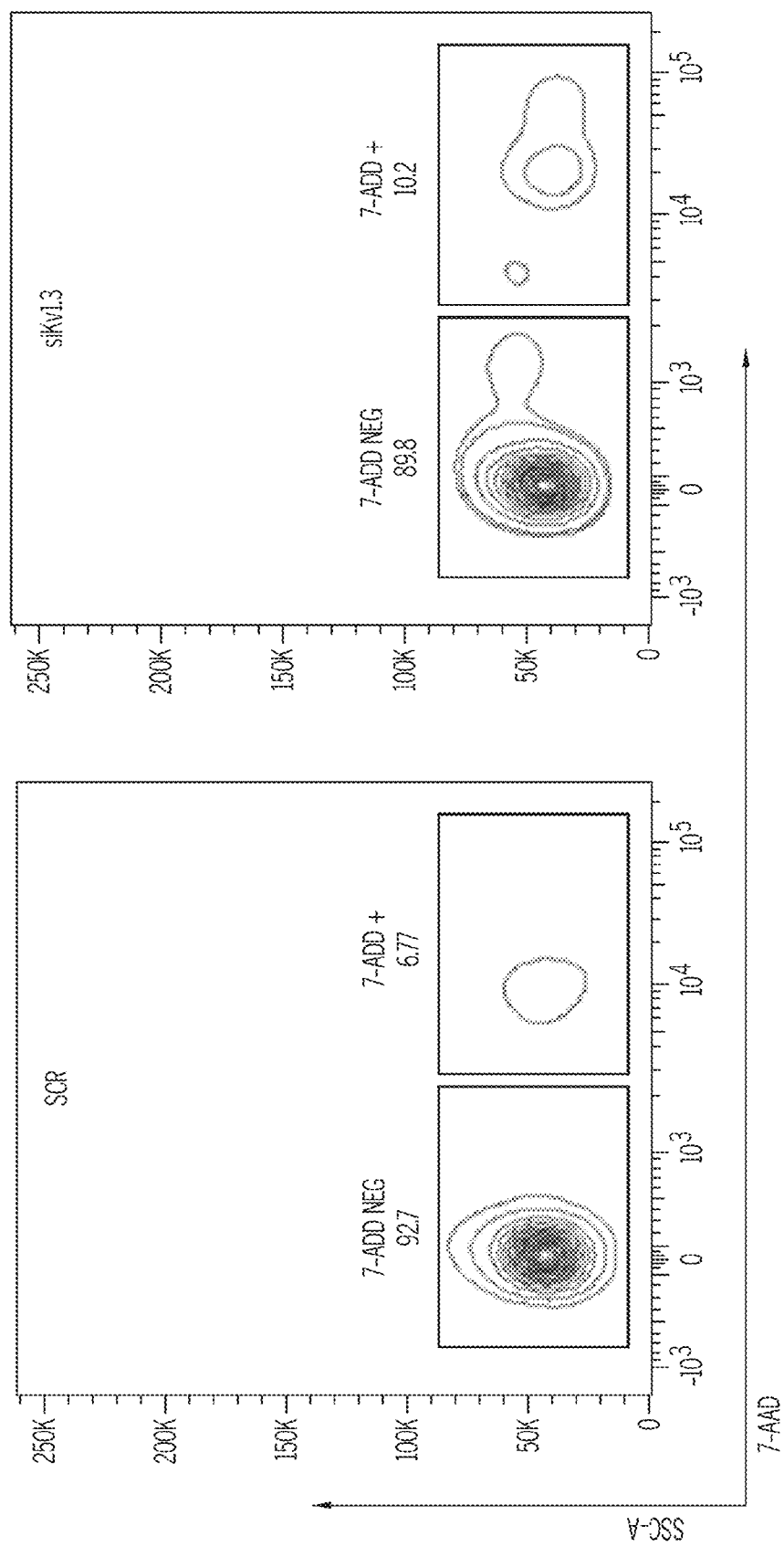
FIG. 21. Graphical representation of data showing viability for cells shown in FIG. 20 as measured by flow cytometry using the nuclear dye 7-AAD.

FIG. 18 sets forth a flow cytometry analysis for CD45RO expression in CD3$^+$ cells isolated from one SLE patient incubated with null-, scr- or siKv1.3-NPs and then activated with TG. As depicted, $T_M$(CD45RO$^+$) and CD45RO$^-$ populations were identified by drawing rectangle gates. FIG. 19 is a graphical representation of the ratio CD45RO$^+$/CD45RO$^-$ in activated CD3 cells isolated from three SLE patients.

iv) Kv1.3-NPs decrease CD45RO expression in CD4$^+T_M$ cells and switch the cell phenotype from CD45RA$^-$ to CD45RA$^+$ FIG. 20 sets forth results of flow cytometry experiments for CD45RO and CD45RA expression in CD4$^+T_M$ cells isolated from a healthy donor and incubated with either scr- or siKv1.3-NPs and then activated with TG. FIG. 21 shows viability for cells shown in FIG. 20 measured by flow cytometry using the nuclear dye 7-AAD.

The foregoing example demonstrates that (1) Kv1.3-NPs selectively target $T_M$ cells from healthy donors resulting in decreased Ca$^{2+}$ influx, inhibition of NFAT nuclear translocation, decreased CD40L expression, and induction of memory loss, i.e. reversion of CD45RO$^+$/CD45RA$^-$ cells to CD45RO$^-$/CD45RA$^+$, and (2) Kv1.3-NPs selectively target $T_M$ cells from SLE patient donors resulting in decreased CD40L expression and decreased CD45RO expression.

The present experiments as well as ongoing empirical studies by the investigators support therapeutic efficacy in the treatment of autoimmune disorders characterized by hyperactive or over expression of $T_M$ cells, exemplified by SLE. The demonstrated reduction in Ca$^{2+}$ influx results in a decrease in $T_M$ hyperactivity and a decrease in Ca$^{2+}$ dependent CD40L expression in $T_M$ cells, which prevents B cell activation and autoantibody production. The demonstrated selectivity for a specific T cell subset overcomes the known problem of systemic inhibition associated with administration of Kv1.3 channel blockers.

It is expressly contemplated that each of the various aspects, embodiments, and features thereof described herein may be freely combined with any or all other aspects, embodiments, and features. The resulting aspects and embodiments (e.g., compositions and methods) are within the scope of the invention. It should be understood that headings herein are provided for purposes of convenience and do not imply any limitation on content included below such heading or the use of such content in combination with content included below other headings.

All articles, books, patent applications, patents, other publications mentioned in this application are incorporated herein by reference. In the event of a conflict between the specification and any of the incorporated references the specification (including any amendments thereto) shall control. Unless otherwise indicated, art-accepted meanings of terms and abbreviations are used herein.

In the claims articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. It is to be understood that the invention encompasses all variations, combinations, and permutations in which one or more limitations, elements, clauses, descriptive terms, etc., from one or more of the listed claims is introduced into another claim. For example, any claim that is dependent on another claim may be modified to include one or more elements, limitations, clauses, or descriptive terms, found in any other claim that is dependent on the same base claim. Furthermore, where the claims recite a composition, it is to be understood that methods of using the composition according to any of the methods disclosed herein, and methods of making the composition, are included within the scope of the invention, unless otherwise indicated or unless it would be evident to one of ordinary skill in the art that a contradiction or inconsistency would arise.

Where elements are presented as lists, it is to be understood that each subgroup of the elements is also disclosed, and any element(s) may be removed from the group. The invention provides all such embodiments.

The terms "approximately" or "about" in reference to a number generally include numbers that fall within ±10%, in some embodiments ±5%, in some embodiments ±1%, in some embodiments, ±0.5% in some embodiments, of the number unless otherwise stated or otherwise evident from the context (except where such number would impermissibly exceed 100% of a possible value). Where ranges are given, endpoints are included. Furthermore, it is to be understood that unless otherwise indicated or otherwise evident from the context and understanding of one of ordinary skill in the art, values that are expressed as ranges may assume any specific value or subrange within the stated ranges in different embodiments of the invention, to the tenth of the unit of the lower limit of the range, unless the context clearly dictates otherwise. Any one or more embodiment(s), element(s), feature(s), aspect(s), component(s) etc., of the present invention may be explicitly excluded from any one or more of the claims.

Those skilled in the art will recognize, or be able to ascertain using no more than routine experimentation, many equivalents to the specific embodiments of the invention described and exemplified herein. The scope of the present invention is not intended to be limited to the above Detailed Description and Examples, but rather is as set forth in the appended claims.

What is claimed:

1. A pharmaceutical composition comprising: lipid nanovesicles functionalized with surface-bound antibody selective for a membrane protein unique to a target subset of immune system cells; and siRNA effective for inhibiting expression of an ion channel of the target subset cells upon transfection, said siRNA encapsulated within the lipid nanovesicle.

2. The composition according to claim 1, wherein the immune system cells are T-cells, the target subset of the T-cells is a CD45RO positive isoform, and the antibody comprises anti-CD45RO.

3. The composition according to claim 2, wherein the T-cell comprises a memory T ($T_M$) cell.

4. The composition according to claim 2, wherein the antibody comprises monoclonal antibody.

5. The composition according to 1, wherein the ion channel comprises Kv1.3.

6. The composition according to claim 1, wherein the siRNA comprises 19-25 nucleotide Kv1.3-specific siRNA.

7. The composition according to claim 6, wherein the siRNA is selected from the group consisting of GUAACUCGACUCUGAGUAAtt (SEQ ID NO: 1), UUACUCAGAGUCGAGUUACtt (SEQ ID NO: 2), CUUACCCUCUCUCUCUUAAtt (SEQ ID NO: 3), UUAAGAGAGAGAGGGUAAGtt (SEQ ID NO: 4), GAUGGACCUUUCAACGUUAtt (SEQ ID NO: 5), UAACGUUGAAAGGUCCAUCtt (SEQ ID NO: 6), and duplexes thereof.

8. The composition according to claim 1, formulated for intravenous administration.

* * * * *

SEQUENCE LISTING

```
<160> NUMBER OF SEQ ID NOS: 6

<210> SEQ ID NO 1
<211> LENGTH: 19
<212> TYPE: RNA
<213> ORGANISM: artificial
<220> FEATURE:
<223> OTHER INFORMATION: Kv1.3-specific siRNA

<400> SEQUENCE: 1
guaacucgac ucugaguaa                                                  19

<210> SEQ ID NO 2
<211> LENGTH: 19
<212> TYPE: RNA
<213> ORGANISM: artificial
<220> FEATURE:
<223> OTHER INFORMATION: Kv1.3-specific siRNA

<400> SEQUENCE: 2
uuacucagag ucgaguuac                                                  19

<210> SEQ ID NO 3
<211> LENGTH: 19
<212> TYPE: RNA
<213> ORGANISM: artificial
<220> FEATURE:
<223> OTHER INFORMATION: Kv1.3-specific siRNA

<400> SEQUENCE: 3
cuuacccucu cucucuuaa                                                  19

<210> SEQ ID NO 4
<211> LENGTH: 19
<212> TYPE: RNA
<213> ORGANISM: artificial
<220> FEATURE:
<223> OTHER INFORMATION: Kv1.3-specific siRNA

<400> SEQUENCE: 4
```

-continued

```
uuaagagaga gaggguaag                                                 19

<210> SEQ ID NO 5
<211> LENGTH: 19
<212> TYPE: RNA
<213> ORGANISM: artificial
<220> FEATURE:
<223> OTHER INFORMATION: Kv1.3-specific siRNA

<400> SEQUENCE: 5
gauggaccuu ucaacguua                                                 19

<210> SEQ ID NO 6
<211> LENGTH: 19
<212> TYPE: RNA
<213> ORGANISM: artificial
<220> FEATURE:
<223> OTHER INFORMATION: Kv1.3-specific siRNA

<400> SEQUENCE: 6
uaacguugaa agguccauc                                                 19
```